(12) United States Patent
Stefanski et al.

(10) Patent No.: US 10,391,258 B2
(45) Date of Patent: Aug. 27, 2019

(54) SETTING MECHANISM

(71) Applicant: COPERNICUS SP. Z O.O., Szczecin (PL)

(72) Inventors: Adam Stefanski, Gniezno (PL); Mateusz Wilczek, Szczecin (PL); Alberto Lozano Platonoff, Szczecin (PL)

(73) Assignee: COPERNICUS SP. Z O.O., Szczecin (PL)

( * ) Notice: Subject to any disclaimer, the term of this patent is extended or adjusted under 35 U.S.C. 154(b) by 0 days.

(21) Appl. No.: 15/952,475

(22) Filed: Apr. 13, 2018

(65) Prior Publication Data

US 2018/0228981 A1 Aug. 16, 2018

Related U.S. Application Data

(63) Continuation of application No. PCT/EP2016/074756, filed on Oct. 14, 2016.

(30) Foreign Application Priority Data

Oct. 15, 2015 (PL) .......................................... 414382

(51) Int. Cl.
  *A61M 5/20* (2006.01)
  *A61M 5/31* (2006.01)
  *A61M 5/315* (2006.01)

(52) U.S. Cl.
  CPC .......... *A61M 5/31585* (2013.01); *A61M 5/20* (2013.01); *A61M 5/2033* (2013.01);
  (Continued)

(58) Field of Classification Search
  CPC .. A61M 5/31585; A61M 5/20; A61M 5/2033; A61M 5/31535; A61M 5/31538;
  (Continued)

(56) References Cited

U.S. PATENT DOCUMENTS

| 2,667,252 A | 1/1954 | Maybach |
| 4,883,472 A | 11/1989 | Michel |

(Continued)

FOREIGN PATENT DOCUMENTS

| CN | 1277558 A | 12/2000 |
| CN | 1509193 A | 6/2004 |

(Continued)

OTHER PUBLICATIONS

International Search Report (PCT/ISA/210) dated Jan. 2, 2017, by the Japanese Patent Office as the International Searching Authority for International Application No. PCT/EP2016/074756.

(Continued)

*Primary Examiner* — Laura A Bouchelle
*Assistant Examiner* — Dung T Ulsh
(74) *Attorney, Agent, or Firm* — Buchanan Ingersoll & Rooney PC

(57) ABSTRACT

A setting mechanism for a dosing device, in particular for a device for dosing pharmaceutical or therapeutic substances, the setting mechanism including: a controlling assembly for connecting the setting mechanism with a dose setting element of the dosing device; a driving assembly for connecting the setting mechanism with a driving element of the dosing device; a dosing assembly for connecting the setting mechanism with a dosing element of the dosing device. The controlling assembly is coupled with the dosing assembly by a spring element, which can deform from a coupled position to a decoupled position during rotation of the dose setting element. The spring element is configured to allow a displacement of the controlling assembly with respect to the dosing assembly. In the coupled position the spring element is configured to block a rotation of the controlling assembly with respect to the dosing assembly.

20 Claims, 29 Drawing Sheets

(52) U.S. Cl.
CPC .... *A61M 5/31535* (2013.01); *A61M 5/31538* (2013.01); *A61M 5/31553* (2013.01); *A61M 5/31583* (2013.01); *A61M 2005/3126* (2013.01)

(58) Field of Classification Search
CPC .......... A61M 5/31553; A61M 5/31583; A61M 2005/2073; A61M 2005/208; A61M 5/31578; A61M 5/3158
See application file for complete search history.

(56) References Cited

U.S. PATENT DOCUMENTS

| | | | |
|---|---|---|---|
| 5,104,380 | A | 4/1992 | Holman et al. |
| 5,503,627 | A | 4/1996 | McKinnon et al. |
| 5,626,566 | A | 5/1997 | Petersen et al. |
| 5,674,204 | A | 10/1997 | Chanoch |
| 6,004,297 | A | 12/1999 | Steenfeldt-Jensen et al. |
| 6,048,336 | A | 4/2000 | Gabriel |
| 6,235,004 | B1 | 5/2001 | Steenfeldt-Jensen et al. |
| 6,899,699 | B2 | 5/2005 | Enggaard |
| 6,936,032 | B1 | 8/2005 | Bush, Jr. et al. |
| 8,096,978 | B2 | 1/2012 | Markussen |
| 2002/0120235 | A1 | 8/2002 | Enggaard |
| 2005/0033224 | A1 | 2/2005 | Kirchhofer et al. |
| 2005/0137534 | A1 | 6/2005 | Hommann |
| 2005/0137571 | A1 | 6/2005 | Hammann |
| 2005/0197625 | A1 | 9/2005 | Haueter et al. |
| 2005/0261634 | A1 | 11/2005 | Karlsson |
| 2006/0258988 | A1 | 11/2006 | Keitel et al. |
| 2007/0088288 | A1 | 4/2007 | Barron et al. |
| 2007/0129687 | A1 | 6/2007 | Marshall et al. |
| 2007/0244436 | A1 | 10/2007 | Saiki |
| 2008/0306445 | A1 | 12/2008 | Burren et al. |
| 2009/0054839 | A1 | 2/2009 | Moller et al. |
| 2009/0054851 | A1 | 2/2009 | Radmer et al. |
| 2009/0254047 | A1 | 10/2009 | Thogersen et al. |
| 2009/0275914 | A1 | 11/2009 | Harms et al. |
| 2009/0299297 | A1 | 12/2009 | Moller et al. |
| 2011/0224622 | A1 | 9/2011 | Karlsson |
| 2012/0197207 | A1 | 8/2012 | Stefanski |
| 2012/0209208 | A1 | 8/2012 | Stefanski |
| 2014/0025016 | A1 | 1/2014 | Plumptre |
| 2014/0303563 | A1 | 10/2014 | Moeller et al. |
| 2014/0350484 | A1* | 11/2014 | Kohlbrenner .......... A61M 5/20 604/222 |
| 2015/0025471 | A1 | 1/2015 | Enggaard |
| 2015/0045737 | A1 | 2/2015 | Stefanski |
| 2015/0051551 | A1 | 2/2015 | Hirschel et al. |
| 2015/0112274 | A1 | 4/2015 | Quinn et al. |
| 2015/0148754 | A1* | 5/2015 | Eich .................. A61M 5/20 604/235 |
| 2016/0101236 | A1 | 4/2016 | Stefanski |
| 2016/0101237 | A1 | 4/2016 | Stefanski |
| 2017/0136182 | A1 | 5/2017 | Marsh et al. |
| 2018/0008777 | A1 | 1/2018 | Stefanski |

FOREIGN PATENT DOCUMENTS

| | | |
|---|---|---|
| CN | 1678362 A | 10/2005 |
| CN | 101033580 A | 9/2007 |
| CN | 101039712 A | 9/2007 |
| CN | 101115520 A | 1/2008 |
| CN | 101262899 A | 9/2008 |
| CN | 203043167 U | 7/2013 |
| EP | 0327910 A2 | 8/1989 |
| EP | 0338806 A2 | 10/1989 |
| EP | 0450905 A1 | 10/1991 |
| EP | 0554996 A1 | 8/1993 |
| EP | 0897728 A1 | 2/1999 |
| EP | 1351732 B1 | 6/2005 |
| EP | 1645301 A1 | 4/2006 |
| EP | 1458440 B1 | 4/2007 |
| EP | 1926514 B1 | 12/2008 |
| EP | 1954337 B1 | 1/2011 |
| EP | 2274032 B1 | 8/2012 |
| EP | 2451508 B1 | 11/2013 |
| JP | 63-501271 A | 5/1988 |
| JP | 02-71578 A | 3/1990 |
| JP | 2008-517233 A | 5/2008 |
| JP | 2008-529690 A | 8/2008 |
| JP | 2008-541932 A | 11/2008 |
| JP | 2009-517157 A | 4/2009 |
| JP | 2014-083398 A | 5/2014 |
| PL | 191327 B1 | 4/2006 |
| PL | 211266 B1 | 4/2012 |
| PL | 214934 B1 | 9/2013 |
| PL | 214935 B1 | 9/2013 |
| PL | 215310 B1 | 11/2013 |
| WO | WO 1989/007463 A1 | 8/1989 |
| WO | WO 92/19297 A1 | 11/1992 |
| WO | WO 1998/039041 A1 | 9/1998 |
| WO | WO 99/38554 A1 | 8/1999 |
| WO | WO 00/62847 A1 | 10/2000 |
| WO | WO 2001/030425 A1 | 5/2001 |
| WO | WO 2001/072361 A1 | 10/2001 |
| WO | WO 2001/095959 A1 | 12/2001 |
| WO | WO 2004/024218 A1 | 3/2004 |
| WO | WO 2005/046770 A1 | 5/2005 |
| WO | WO 2006/037434 A1 | 4/2006 |
| WO | WO 2006/045523 A1 | 5/2006 |
| WO | WO 2006/045526 A1 | 5/2006 |
| WO | WO 2006/045528 A1 | 5/2006 |
| WO | WO 2006/084876 A1 | 8/2006 |
| WO | WO 2006/126902 A1 | 11/2006 |
| WO | WO 2006/130100 A1 | 12/2006 |
| WO | 2008116766 A1 | 10/2008 |
| WO | WO 2009/039851 A1 | 4/2009 |
| WO | WO 2009/105909 A1 | 9/2009 |
| WO | WO 2010/089417 A2 | 8/2010 |
| WO | 2010149717 A1 | 12/2010 |
| WO | WO 2011/025448 A1 | 3/2011 |
| WO | 2012063061 A2 | 5/2012 |
| WO | WO 2012/154110 A1 | 11/2012 |
| WO | WO 2013/119132 A1 | 8/2013 |
| WO | 2013137893 A1 | 9/2013 |
| WO | 2013167869 A1 | 11/2013 |
| WO | 2013178372 A1 | 12/2013 |
| WO | WO 2014/033195 A1 | 3/2014 |
| WO | 2014060369 A1 | 4/2014 |
| WO | 2014166921 A1 | 10/2014 |
| WO | 2014170177 A1 | 10/2014 |
| WO | WO 2015/032772 A1 | 3/2015 |
| WO | WO 2015/055640 A1 | 4/2015 |
| WO | WO 2015/071289 A1 | 5/2015 |
| WO | 2015140086 A1 | 9/2015 |
| WO | 2016055505 A1 | 4/2016 |
| WO | 2016107790 A1 | 7/2016 |
| WO | 2016135237 A1 | 9/2016 |
| WO | 2017055492 A1 | 4/2017 |
| WO | 2017060426 A1 | 4/2017 |
| WO | 2017064275 A1 | 4/2017 |

OTHER PUBLICATIONS

Written Opinion (PCT/ISA/237) dated Jan. 2, 2017, by the Japanese Patent Office as the International Searching Authority for International Application No. PCT/EP2016/074756.

* cited by examiner

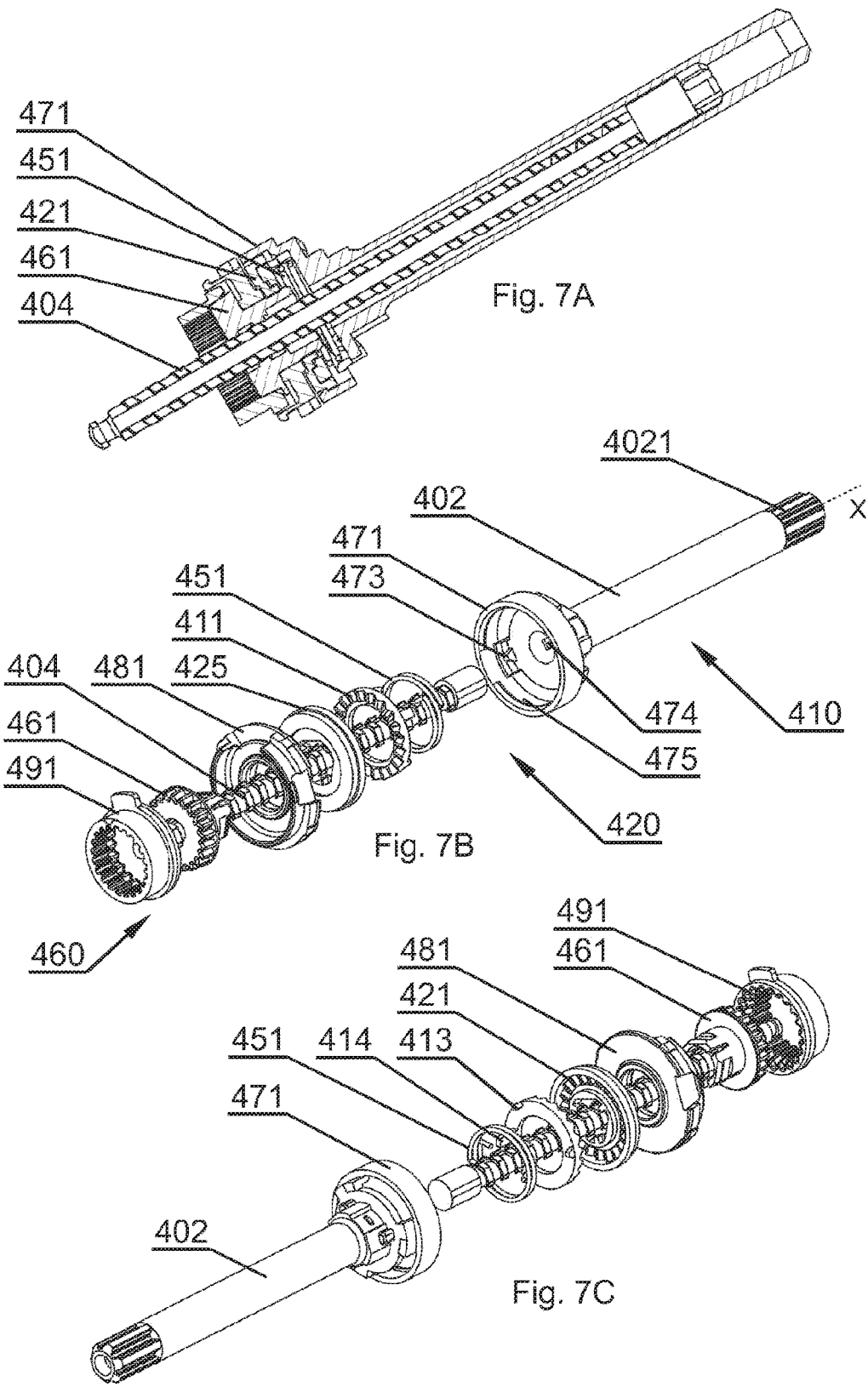

SETTING MECHANISM

TECHNICAL FIELD

The present application relates to devices, actuating assemblies, delivery systems and setting mechanisms, for use in particular for dosing, including applicators of pharmaceutical or therapeutic substances, such as insulin. In particular, it relates to devices capable of reducing a set dose.

BACKGROUND

The currently known applicators of pharmaceutical or therapeutic substances comprise various setting mechanisms for setting an amount of a substance to be dosed. Some of these mechanisms enable reducing the set dose. A number of examples of these types of mechanisms will be discussed below. Dosing devices are typically devices for injecting (called injectors). Some of these devices are provided with a housing resembling a pen (called pen injectors).

A European patent EP1351732B1 discloses a device for setting a dose for use with a reservoir filled with a liquid, wherein the device for setting the dose is adapted for repetitive injection of individually set liquid doses from the reservoir. The device comprises a housing, a driving element, spring means, dosing assembly and releasable lock means coupled with the housing for holding the device in a set position regardless of the operation of the spring means.

A European patent EP1926514B1 discloses an injecting device comprising a housing with a reservoir for a product to be injected, a drive knob, which, after setting a product dose, can be moved with respect to the housing in a direction in which it increases the dose, and in a direction providing a correction of the dose, a delivery (delivering) element for emptying the set dose, a slipping clutch with a detent element and a counter detent element, which come into mutual positive and non-positive engagement in discrete latching positions of the housing to arrest the actuating head during a movement in the dose setting direction or in the dose correcting direction, and a spring element, which applies a spring force opposing the movement of the actuating head in at least one direction.

A Polish patent PL211266B1 discloses a dose correction mechanism of an automatic applicator, comprising a double-clutch assembly for setting and correcting the set dose, constituting a coupling sleeve connected with a ratchet sleeve and connected with a nut, wherein the coupling sleeve is coupled radially with the ratchet sleeve by a control recess and a projection and coupled with a driving nut by latching arms passing through through-holes of the coupling sleeve.

A PCT application WO2006/045526 discloses a dial-down mechanism for an injection device comprising a torsion spring for assisting injection of a dose of medicament from the injection device, the dial-down mechanism comprising dial-up cam arranged to receive and engage with a dial-up key, wherein the dial-up cam and the dial-up key are adapted to, upon rotation of a dose setting member in a first direction, cooperate to strain the torsion spring of the injection device, and a dial-down cam arranged to receive and engage with a dial-down key.

A US patent application US2015112274A1 discloses a medication injection pen, comprising a housing; a dose set knob rotatable with respect to said housing; a brake assembly disposed in said housing and having a ratchet member; and a driver including at least one external tooth engaging said ratchet member, wherein said engagement between said ratchet member and said at least one external tooth substantially prevents said driver from rotating with respect to said dose set knob during dose setting and dose correcting, and said engagement between said ratchet member and said at least one external tooth allows said driver to rotate with said dose set knob during an injection.

A PCT application WO2014033195 discloses a reusable device for delivering a drug, for selecting and dispensing a number of user variable doses of a medicament, comprising a housing, a cartridge holder, a piston rod, a driver, a display member for indicating a set dose, a clutch and a button.

A PCT application WO2015055640 discloses a drug delivery device comprising a cartridge comprising a cylindrical body portion, an outlet portion and an axially displaceable piston, an expelling assembly, a rotatable driver assembly allowing a user to set a dose amount to be expelled and strain the drive spring correspondingly, a ratchet allowing the driver assembly to be rotated from an initial position in a first direction and held in a rotational position corresponding to a set dose.

There is a need to improve the known devices to eliminate at least part of the problems as described above and to provide alternative solutions. The problems present in the devices known so far include, among others: a large number of elements, highly complicated design, high manufacturing costs, insufficient durability, a relatively low strength (in particular, elements that are fragile and brittle during manufacture and use), insufficient dosing accuracy, problems with uncontrolled outdropping of the substance, and insufficient operating comfort for a user. Not all solutions meet technological manufacturing regimes, and they do not ensure patient safety during use. Moreover, in case of mechanisms based on a number of cam-and-wedge couplings, in relation to small-dimension devices, e.g. injection devices, it has been shown that such cam-and-wedge elements of small dimensions are not reliable—they tend to break during manufacture or during use.

In the known devices, forces required to set and correct the dose are different, in particular the force needed to reduce (correct) the dose is greater than the force to set the dose. Furthermore, the forces can increase substantially along with increasing the set dose. Some solutions require a ratchet as an element necessary for operation. Other solutions do not have a driving spring, and are not automatic.

Therefore, there is a need to provide a mechanism, which would solve at least part of the above-mentioned problems and achieve at least partially the following effects: lower number of elements, greater design simplicity, lower manufacturing costs, desirable strength during manufacture and use, reliability, desirable durability, desirable dosing accuracy (in particular, complying with ISO 11608-1:2014), little outdropping, desirable operating comfort for a user, ease of operation, small resistance during dose setting and/or dose correcting, providing substantially equal force during dose setting and correcting, a mechanism devoid of a ratchet or cams, providing a possibility of cooperation with spring means for effecting a movement of a piston rod, providing automatic dose supply and requiring a smaller force from a user.

There is also a need to provide an improved method for delivering substances, in particular pharmacological substances, in particular using the mechanism as disclosed herein.

SUMMARY

There is disclosed a setting mechanism for a dosing device, in particular for a device for dosing pharmaceutical or therapeutic substances, for example for a reusable injector, in particular for insulin. The setting mechanism may comprise a controlling assembly for connecting the setting mechanism with a dose setting element of the dosing device. The setting mechanism may further comprise a driving assembly for connecting the setting mechanism with a driving element of the dosing device. The setting mechanism may further comprise a dosing assembly for connecting the setting mechanism with a dosing element of the dosing device. The controlling assembly can be coupled with the dosing assembly by a spring element, which can deform from a coupled position to a decoupled position during rotation of the dose setting element, wherein the spring element is configured to allow a displacement of the controlling assembly with respect to the dosing assembly, and wherein in the coupled position the spring element is configured to block a rotation of the controlling assembly with respect to the dosing assembly.

In other words, there is disclosed a setting mechanism for a dosing device, in particular for dosing pharmaceutical or therapeutic liquids, for example for a reusable injector, in particular for insulin. The setting mechanism may comprise at least four interconnected rotatable elements. At least two rotatable elements can be rotatable during setting or correcting a dose for the dosing device. A first rotatable element can be a receiving element and comprises corrugations. A second rotatable element or a third rotatable element or a fourth rotatable element may comprise corrugations coupled with the corrugations of the first rotatable element. Said corrugations can be shaped such that they enable rotation of said at least four rotatable elements during delivering the dose by the dosing device.

The rotatable elements may form: a controlling assembly for connecting the setting mechanism with a dose setting element of the dosing device; a driving assembly for connecting the setting mechanism with a driving element of the dosing device; and a dosing assembly for connecting the setting mechanism with a dosing element of the dosing device. The controlling assembly can be coupled with the dosing assembly by a spring element, which during rotation of the dose setting knob can deform from a coupled position to a decoupled position, wherein in the decoupled position the spring element can be configured to allow a movement of the controlling assembly with respect to the dosing assembly, and wherein in the coupled position the spring element can be configured to block a rotation of the controlling assembly with respect to the dosing assembly.

The mechanism may comprise at least two, and preferably at least three, rotatable elements that are rotatable with respect to the dosing device which are substantially fixed with respect to each other.

The mechanism may comprise at least one rotatable element movable by sliding, axially or radially.

The spring element can be separate from the driving element of the dosing device.

The controlling assembly and the dosing assembly may comprise corrugated elements, which in the coupled position abut each other at least partially, and which are spaced apart in the decoupled position.

The corrugated elements may comprise axially protruding protrusions.

The corrugated elements may comprise radially protruding protrusions.

The corrugated elements may comprise friction surfaces or latching surfaces or toothed surfaces or connecting surfaces.

The corrugated elements cooperating with each other can be co-axial and have corrugations arranged on parallel planes.

The mechanism may comprise at least two rows or series of corrugated elements that are arranged, preferably in a circular arrangement, on rotatable disc elements, preferably having a common centering axis, which abut each other or which are spaced apart.

The corrugations of the at least two rows or series of the corrugated elements may have different heights or different angles of inclination.

The at least two rows or series of corrugated elements can be coupled with different coupling strengths (in a special case, the coupling strength of the corrugated elements can be equal).

The corrugated elements can abut each other during rotation of the driving element in a dose setting direction, and separate from each other during rotation of the driving element in a dose correcting direction.

The number of corrugations in the corrugated elements of the controlling assembly can be different than the number of corrugations in the corrugated elements of the dosing assembly.

The mechanism may comprise at least one corrugated element connected indirectly or directly with the controlling assembly, preferably by a coupling sleeve or by a clutch.

The spring element can rotate with respect to the dosing device in accordance with the rotation of the dose setting element of the dosing device in the dose setting direction and/or in the dose correcting direction.

The dose setting element can be connected, preferably directly, substantially with the same coupling element that couples the setting mechanism.

The dosing assembly may comprise a nut connected with the dosing element, preferably a piston, of the dosing device, wherein the nut is connected with at least one rotatable element of the controlling assembly and/or of the dosing assembly.

The controlling assembly and the dosing assembly may have at least one common element.

The spring element can be a torsion spring, a compression spring or a torsion-compression spring.

The spring element can be radially deformable.

The spring element can be axially deformable.

The spring element can be an elastic fragment of the rotatable element that can be rotatable with respect to the dosing device.

The rotatable elements can be configured such that they define a force acting during a movement in a direction corresponding to a dose setting substantially equal to a force ensuring a movement in a direction opposite to the dose setting direction.

At least two rotatable elements, and preferably three rotatable elements, of the setting mechanism can be substantially immovable with respect to each other.

The mechanism may comprise a nut for driving the piston rod of the dosing device, the nut being connected with a first or a second driving element.

The controlling element can be a first coupling disc, coaxial with the main axis of the mechanism, with corrugations, preferably with teeth arranged on a surface perpendicular to the main axis of the mechanism. The driving element can be a second coupling disc, coaxial with the main axis of the mechanism, with corrugations, preferably with teeth directed opposite to the teeth of the first disc. The first coupling disc can be movable axially with respect to the second disc along the main axis of the mechanism during the rotation of the controlling element so that their mutual axial position changes from the coupled position to the decoupled position. The spring element can be deformable axially.

The controlling element can be a disc with protrusions.

The driving element can be a disc with teeth arranged around the main axis.

Furthermore, the mechanism may comprise a first coupling disc, which can be coaxial with the main axis of the mechanism and can be connected to the knob for setting the dose.

The mechanism may comprise a second coupling disc, which can be coaxial with the main axis of the mechanism, and may have teeth directed in a direction opposite to the direction of teeth of the first coupling disc and can be connected to the driving spring for expelling the dose.

The mechanism may comprise a third coupling disc, which can be coaxial with the main axis of the mechanism, and may have teeth directed in the same direction as the teeth of the first coupling disc and can be movable axially along the main axis X of the mechanism.

The mechanism may comprise a locking element, which may have protrusions for coupling slidably with the inlets in the clutch, so that the clutch can be immovable rotationally with respect to the locking element, but can move axially with respect to the locking element, and can be attached using a latch to the latch of the clutch disc of the spring.

The mechanism may comprise a nut, which can be adapted to rotate the dose setting piston rod and can be connected rotationally with the locking element.

The mechanism may comprise a spring, which can be mounted between the third coupling disc and the locking element, and generates a force pressing the third coupling disc in the direction of the second coupling disc.

The first coupling disc can be connected with the knob for dose setting, by means of a rod, with respect to which the first coupling disc can be movable axially with respect to the main axis of the mechanism.

Furthermore, the mechanism may comprise a first coupling disc, which can be coaxial with the main axis of the mechanism, which can be controlled by the knob for dose setting and can be connected to the driving spring for dose expelling.

The mechanism may comprise a second coupling disc, which can be coaxial with the main axis of the mechanism, and may have teeth directed in the opposite direction to the direction of the teeth of the first coupling disc.

The mechanism may comprise a third coupling disc, which can be coaxial with the main axis of the mechanism, may have teeth directed in the same direction as the first coupling disc and can be movable axially along the main axis of the mechanism.

The mechanism may comprise a locking assembly, which may have protrusions for coupling slidably with inlets in the first disc, so that the disc can be immovable rotationally with respect to the locking element, but can move axially with respect to the locking element.

The mechanism may comprise a nut, which can be adapted to rotate the dose setting piston rod, and can be connected to a fourth coupling disc, which can be coaxial with the main axis of the mechanism and can be connected rotatably with the controlling element through further coupling discs.

The mechanism may comprise a spring, which can be mounted between the first coupling disc and the controlling element and generates a force pressing the first coupling disc in a direction of the second coupling disc.

Furthermore, the mechanism may comprise a housing, which can be coaxial with the main axis of the mechanism and can be connected with a nut for dose setting.

The mechanism may comprise a first coupling disc, which can be coaxial with the main axis of the mechanism and may have on the side opposite to its teeth a lock in a form of a protrusion, which abuts a lock of the housing for a certain angular position between the first coupling disc and the housing.

The mechanism may comprise a twisting element between the first coupling disc and the housing.

The mechanism may comprise a second coupling disc, which can be coaxial with the main axis of the mechanism and can be coupled with the first coupling disc and may have teeth directed in a direction opposite to the direction of the teeth of the first coupling disc.

The mechanism may comprise a nut, which can be adapted to rotate the dose setting piston rod and can be connected to the second coupling disc non-rotatably and non-movably.

Furthermore, the mechanism may comprise a first coupling disc, which can be coaxial with the main axis of the mechanism, and which can be connected with the dose setting knob, and which may comprise tracks, in which rolling elements are placed.

The mechanism may comprise a second coupling disc, which can be coaxial with the main axis X of the mechanism, which may comprise a spring element for pressing the rolling elements against the track. The track can be coaxial with the main axis of the mechanism, and may comprises recesses of a radius corresponding to the radius of the rolling elements.

The mechanism may comprise a nut, which can be adapted to rotate the dose setting piston rod and can be connected with the track.

The mechanism may comprise a first coupling disc, which can be coaxial with the main axis of the mechanism and can be connected with the dose setting element.

The mechanism may comprise a second coupling disc, which can be coaxial with the main axis of the mechanism, and can be shaped on the inner side of the cylindrical sleeve, which may have an inlet and an outlet, which are limited by a locking element, and which can be coupled with the first coupling disc via teeth of the second coupling disc directed in the direction opposite to the direction of the teeth of the first coupling disc. The teeth can protrude outside the disc in a radial direction pressing elements between the first coupling disc and locking elements for holding the first coupling disc in a middle position, coupled with the second coupling disc.

The mechanism may comprise a nut, which can be adapted to rotate the dose setting piston rod and which can be connected with the second coupling disc.

There is also disclosed a dosing device comprising the setting mechanism as described above and in the example embodiments.

The driving element of the device can be a torsion spring.

The driving element can be further connected to the controlling assembly.

The driving element can be further connected to the dosing assembly.

The device may comprise at least two spring elements, wherein the first spring element is a driving element for delivering a liquid from a liquid container, and wherein the second spring element is an element of the setting mechanism that is configured to act on the assemblies of the setting mechanism during dose setting and/or dose correcting.

The release of energy accumulated in the first spring element may cause the second spring element to undergo a rotation equal to the rotation of the dosing assembly of the setting mechanism.

The presented mechanism can be used in a method for injecting a pharmaceutical substance, particularly comprising steps of: providing a dosing device comprising a reservoir with plurality of doses of the substance; setting a dose of the substance by rotating a dose setting element in a first direction, wherein during dose setting the energy is stored in the device; reducing the set dose by turning the dose setting element in a second direction, wherein during reducing of the dose the energy stored in the device is released.

Storing of the energy in the device can be effected by the setting mechanism, in which the controlling assembly connected with the dose setting element and coupled with the driving assembly for releasing energy stored in the device is set in the decoupled position, in which a movement of the controlling assembly with respect to the dosing assembly is enabled, or in a coupled position wherein a rotation of the controlling assembly with respect to the dosing assembly is blocked.

Storing of the energy in the device can be effected by the setting mechanism, in which at least two elements are rotatable during dose setting or decreasing, and at least four elements are rotatable during dose delivering during releasing of the energy stored in the device.

The setting mechanism can be used in dosing devices of various kinds. In pharmaceutical or therapeutic substance applicators there are used reservoirs comprising a particular substance, which are typically pre-filled, for example having a volume 1.5 or 2.4 or 3.0 ml. The substance can be a liquid or a suspension, comprising a medicine, a vaccine or other ingredients. One example of a substance that is commonly produced or delivered in this manner is insulin and its analogs. Growth hormone, teriparatide, GLP-1 or other substances are also used. Overall, this may cover pharmaceuticals comprising peptides, proteins, small molecules, ingredients obtained biologically, active biological ingredients, hormonal ingredients, genetic ingredients or similar. The device can be used with any of the mentioned substances, or with other substances as well.

The setting mechanism can be used in dosing devices (also known as injectors) of "reusable" or "durable" type, as well as of "pre-filled" or "disposable" type. Reusable devices allow a user to replace a used reservoir with another one. On the other hand, disposable devices are equipped with a reservoir integrated with the device, which is not expected to be replaced. The substance is provided through a needle, mounted on the device, through which the flow occurs through a pierced partition of the reservoir.

The setting mechanism can be used in dosing devices of manual or automatic type. In particular, in automatic devices there is used a driving spring for injecting the pharmacological substance. In a preferred embodiment, the solution provides a possibility of use in an automatic dosing device (an automatic injector), that is in a dosing device, using spring means, preferably a torsion spring for expelling the medicament, preferably by transferring the force onto an axially movable piston, which is preferably connected with a knob. In the injector as presented herein, the spring means acting as the driving spring can be a pre-loaded spring. It is possible to use a relaxed spring.

As spring means (in particular driving spring means), there can be used any kind of means for accumulating energy through deformation, in particular it can include coil springs, spiral springs, clock springs, push springs, torsion springs or elastomeric springs.

The setting mechanism can be used in dosing devices that allow delivering of variable doses, as well as in dosing devices delivering a fixed dose.

The setting mechanism can be used in dosing devices comprising a maximal dose limiter, a stopper or other system allowing for controlling of the last dose or preventing delivery of a dose greater than the one remaining in the reservoir, as for example in injectors known from EP1458440B1 or EP2274032B1.

The setting mechanism can be used in dosing devices, which comprise an indicating mechanism configured to indicate the set dose to the user. The indicating mechanism can encompass given embodiments, or a different indicating mechanism can be used, which is known in the art, e.g. WO2006/045528, US2015112274, WO2006/037434, EP1954337 etc.

The setting mechanism can be used in dosing devices allowing reduction of the set dose. The reduction can be performed by dose resetting, as described for example in WO2013119132. The reduction can also be performed in other ways, using assemblies such as for example these shown in EP1954337 or WO2006126902 or other documents cited therein. In particular, reduction of the dose can allow decreasing by any number of set units. One or several operations lead to reaching of the initial position (normally denoted as 0).

The setting mechanism can be used in dosing devices allowing for selecting a dose only in one direction. For example, locking the movement of one of the discs in a direction opposite to the dose setting direction, locking the movement opposite to the setting on dose setting element or elimination of one or more elements responsible for the movement opposite to the dose setting direction allows providing only one-directional movement of the setting mechanism.

The setting mechanism can be used in a device, in which pressing the releasing button until the end of the injection, wherein stopping of the pressing leads to automatic return of the releasing button to the initial position.

The setting mechanism can be used in dosing devices, in particular for multiple injections of individually set doses from a reservoir, comprising: a housing, a driving element configured to expel a dose of a liquid from a reservoir, spring means. The setting mechanism can be mounted in the housing and can be connected with spring means. The device may comprise a dose setting element movable in a first direction to selected and set position with respect to the spring means, wherein the movement of dose setting element can be accompanied by compression of a spring and wherein the dose setting element can be movable in a second direction so as to selectively regulate the set dose. A latching assembly, holding the injecting device in a set position with respect to the compression of the spring, can be associated with the housing, wherein the latch can be eleasable so as to initiate a controlling element for expelling the set dose from the reservoir, wherein the force of expelling of the set dose can be provided by spring means.

The setting mechanism can be used in dosing devices, comprising a housing, a dose setting mechanism for setting the dose to be delivered from the substance reservoir when the substance reservoir can be coupled with the housing, and a dose delivering mechanism, wherein the dose setting mechanism may comprise a dose setting structure operable to set the initial dose and a dose indicating structure, wherein the dose setting structure and the dose indicating structure can be coupled so as to undergo correlated displacements with respect to the housing during the initial dose setting, appropriately during dose delivering, wherein the correlated displacements during the dose setting are opposite with respect to the correlated displacements during dose delivering, wherein the dose setting structure can be displaced to a prepared dose position in order to set the initial dose, wherein the prepared dose position can be fixed with respect to the housing, and wherein the dose indicating structure can be displaced to a dose stopping position during dose delivering, wherein the dose stopping position can be fixed with respect to the housing, and wherein the dose indicating structure can be selectively displaceable with respect to the housing when the dose setting structure can be in the prepared dose position to allow adjustment of the initial dose and setting the final dose.

The mechanism can be used in a method for assisting a patient with injecting a pharmaceutical substance, which may comprise the steps of: supplying to the patient instructions for using a dosing device comprising a reservoir with plurality of substance doses and a driving element which uses energy accumulated by a patient for expelling the substance from the dosing device; supplying to the patient instructions for setting the substance dose by rotating the dose setting element in a first direction; supplying to the patient instructions that the dose can be decreased by rotating the dose setting element in a second direction; supplying to the patient instructions to push an actuating member of the device, which will release the energy stored in the device during dose setting and will effect the expelling of at least part of the substance from the reservoir (the actuating member can automatically return to the initial position after releasing the contact).

The mechanism can also be used in a method for treating an illness, which requires injection of the medical substance without anyone's assistance, which may comprise supplying to the patient a dosing device comprising a reservoir with plurality of substance doses.

The mechanism can also be used in a method in which an injecting device can be provided, wherein the dose can be selected by rotating a dose setting element in a first direction (a dose setting direction) causing accumulating energy for moving a piston rod and expelling of the set dose from the device, and an optional dose reduction can be effected by moving a dose setting element in a second direction (a dose correcting direction). The release of the energy stored in the device can be effected in particular by using an actuating member (activated or held), preferably axial, up to expelling of the dose, which after crossing a limit value of the force used in order to activate the actuating member, provides substantially a constant velocity of outflow of the substance independently from the extent of crossing the limit value (without taking into account initial movement differentiation and velocity increase until reaching desired velocity).

The mechanism is particularly useful in devices, wherein there is substantially provided a constant time of injection for a particular dose. Preferably, the time for 20 IU injection is within a range from 0.9 to 1.8 second, and for 40 IU the time is within a range from 2.1 to 3.6 seconds. Preferably, the injection force does not exceed 10 N, and preferably is close to 5 N. Preferably, the injection force does not change substantially in accordance with the size of selected (set) dose.

BRIEF DESCRIPTION OF THE FIGURES

The attached drawing includes the following figures:
FIGS. 7A-7E show another embodiment of a mechanism.

DETAILED DESCRIPTION

Figure 1A:
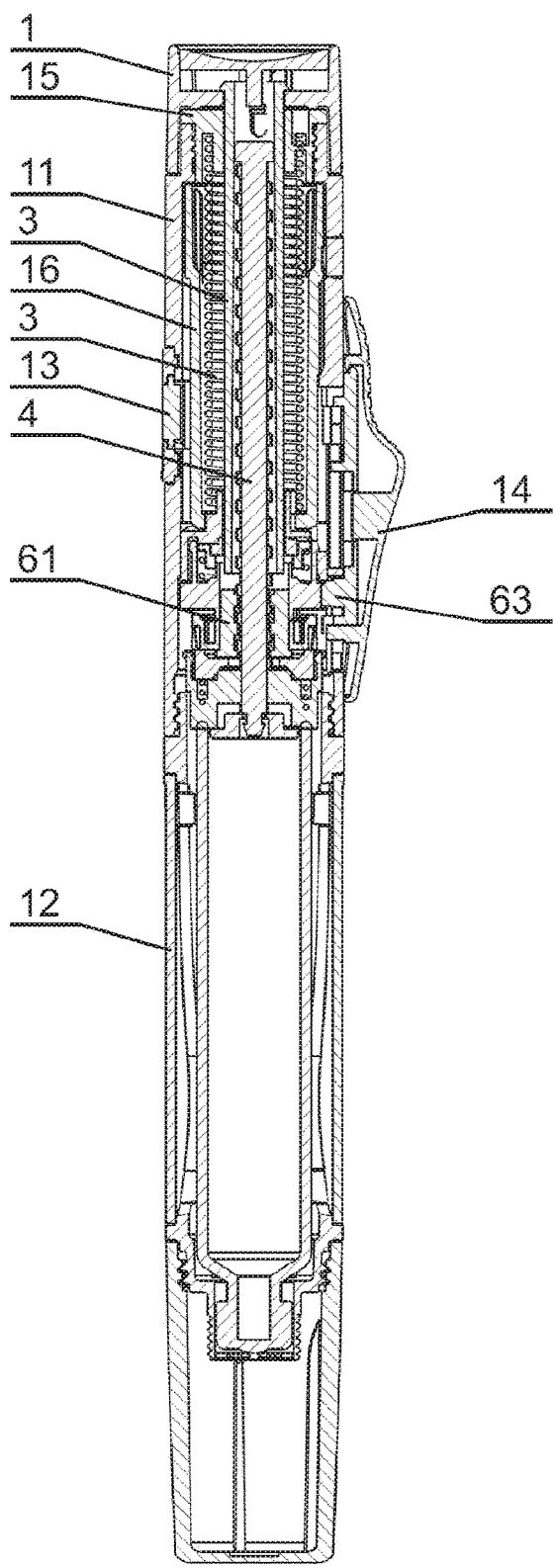
FIGS. 1A-1D show examples of constructions of applicators, in which the setting mechanisms of example embodiments can be used.
Figure 1B:
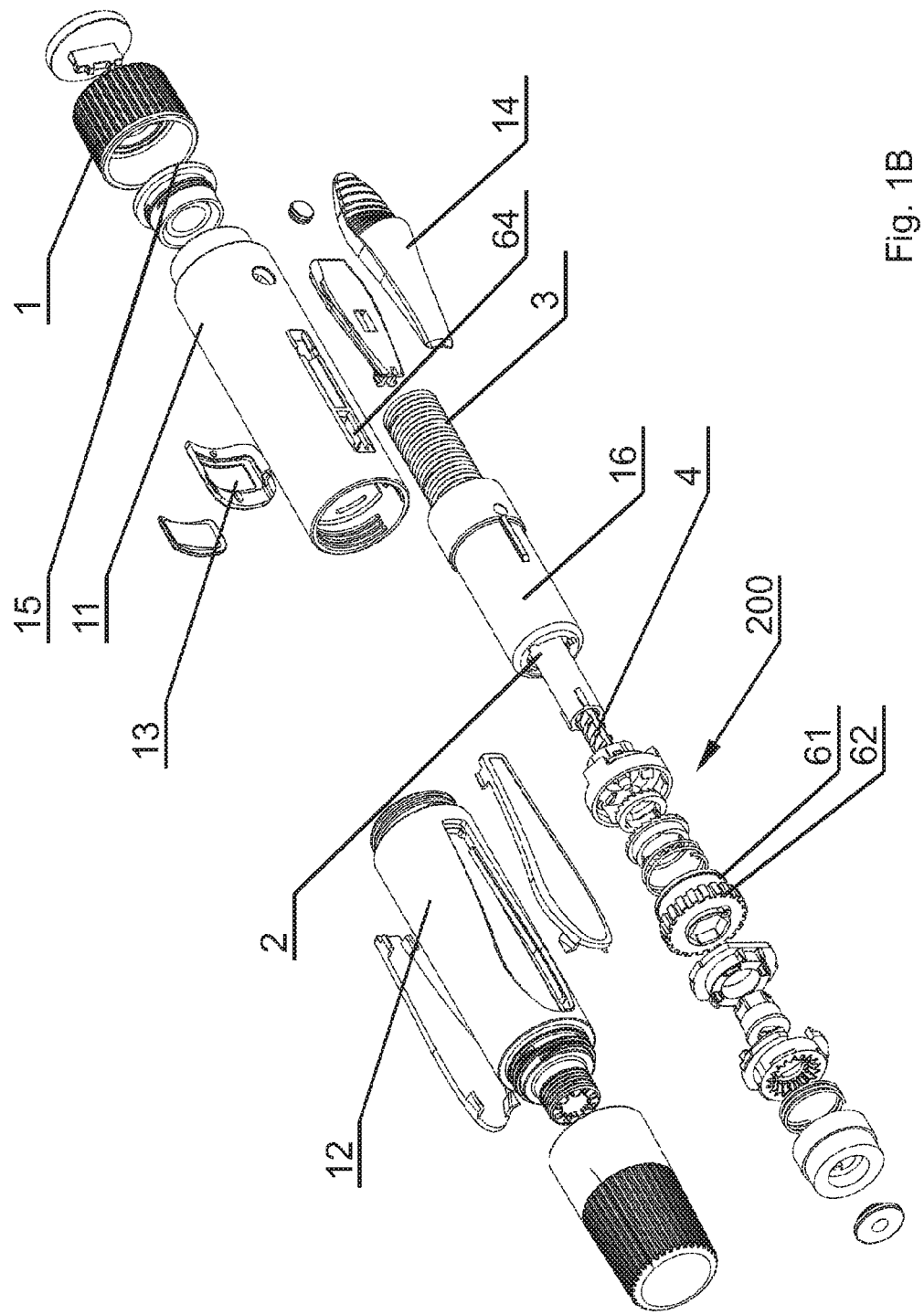

FIGS. 1A, 1B show an example of application of a mechanism in an automatic applicator for liquid pharmaceutical preparations, for example for insulin, for repeated delivery, by injection, of set doses of the liquid preparation from an exchangeable container.

FIG. 1A shows a longitudinal sectional view of the applicator, and FIG. 1B show an exploded view. This type of applicator is disclosed in a patent document PL215310, which explains in details its principles of operation.

The applicator may comprise a two-part body 11 connected with a casing 12 of a container with a liquid pharmaceutical preparation (exchangeable or non-exchangeable; not shown in this drawing). The liquid preparation can be pushed out form the container by a piston rod 4 ended with a piston, connected with a setting mechanism and movable linearly by a setting mechanism which can be of a type as described in details with respect to the embodiments presented below. A setting mechanism 200, such as the one shown in FIGS. 4C-4D, can be used in this applicator. The mechanism can be driven by a driving spring 3, in this example a coil spring. The driving spring 3 can be placed in the body 11 and can be tensioned by a dose setting knob 1. The setting mechanism can be activated by an actuating member assembly 14. A printed scale (not shown on this figure) with a graduation can be placed on a sleeve 16 and can be visible through an inspection opening 13.

The automatic applicator may operate as follows. In case of a reusable injector, in order to replace the liquid preparation container, the casing 12 of the container, connected with the body 11, should be unscrewed. After unscrewing the casing 12 of the container, the lock of the piston rod 4 with respect to the encasing element is decoupled, which is caused by the pressure of the spring, by moving the lock of the piston rod in the axial direction towards the piston rod and detaching special cutouts present in both elements subject to the decoupling. This allows manual retraction of the piston rod 4 by applying a force in the axial direction, thereby pushing it into the body. The tip can be mounted on the piston rod such that they can rotate independently. Because the connection between the piston rod 4 and a driving nut 61 can be effected using a non-self-locking thread, while the piston rod is being pushed in this thread, it automatically screws into the driving nut 61. The force should be exerted onto the piston rod 4 until the piston rod hides completely in the body 11 and allows to install a new container with a liquid preparation.

If the applicator is of a disposable type, then it may comprise a non-exchangeable container, and the casing 12 cannot be unscrewed from the body 11, and the above mentioned aspects can be ignored.

The driving nut 61 and the piston rod 4 can be connected with each other by a thread having a pitch that allows delivering of a right dose of the liquid preparation. Moreover, the driving nut 61 can be mounted in bearing in the encasing element, preferably in a ball bearing.

Next, a needle (not shown) mounted in the casing 12 of the container should be unscrewed (preferably by rotating it anti-clockwise), after which the empty container for the insulin should be removed by sliding it out of the casing 12, and a new container should be installed in this place.

In order to install a new container, it should be slid into the container casing 12, which should be subsequently placed in the body 11 by rotating it clockwise. Next, a new needle should be mounted and the casing 12 should be slid over, which can be a securing nut.

The dose setting can be effected by turning the knob 1 in a dose setting direction, for example clockwise. The currently set dose can be visible on a part of the cylindrical sleeve 16 through a window of the inspection opening 13 in the body 11, which together with the scale, in particular applied linearly below the lock protrusion on a cylindrical sleeve 16, forms an indicating assembly.

The knob 1 can be connected rigidly with a coupling sleeve 2 and when the dose is to be increased, the coupling sleeve 2 can be rotated in the dose setting direction, which causes tensioning of the driving spring by the setting mechanism, in accordance with its operating principle. The setting mechanism can be connected, preferably rigidly, with a spring 3, which can be connected with a lock 15 of the spring 3. The lock 15 of the spring 3 can be connected rigidly with the body 11 protected from rotation.

During dose setting, the driving nut 61 can be immobilized by an actuating member 14 by means of rectangular grooves 62 situated on the circumference of the driving nut 61. A protrusion 63 of the actuating member 14 cooperates with these grooves.

The working range of the applicator can be determined by the lock protrusion situated directly on the circumferential surface of the sleeve 16 and cooperating with the protrusion on the inner part of the cylindrical surface of the body 11, placed under or above the window of the inspection opening 13. These protrusions can be located on the opposite sides and at the same time can be slightly shifted axially. Such location makes it possible to perform one incomplete rotation of the sleeve that may comprise the protrusion.

After setting the dose, the dosing of the liquid preparation can be effected by moving the actuating member 14 towards the needle, wherein the actuating member should be held in a pushed position during the whole time of delivering the substance. The range of the actuating member 14 can be determined by the protrusion 63 in a groove 64 of the body 11. After pushing the actuating member 14, the driving nut 61 is released by decoupling of the toothed ring located on the driving nut 61 and the protrusion 63 located on the actuating member 14. The mechanism starts rotating due to a force of the spring 3. Rotation of the driving nut 61 causes twisting-out of the piston rod 4 through a thread connection. The piston rod 4 before the rotation can be blocked by an inlet on the piston rod lock and a cut-out in the piston rod. The piston rod 4 acts directly on the piston of the container with the liquid preparation, placed in the casing 12 of the container and causes an injection of the substance through the needle, mounted on the casing 12 of the container. At the same time, the movement can be accompanied by retracting the whole setting mechanism to the initial position, i.e. the driving spring can be loosened to initial preload, and the sleeve 16 with the scale returns to the initial position (typically denoted as "0").

After finishing the dosing, the actuating member 14 can be released, which will automatically return to its initial position due to the spring, which can be located directly under the actuating member 14 assembly, and will block the driving nut 61 again.

Example of Application

Figure 1C:
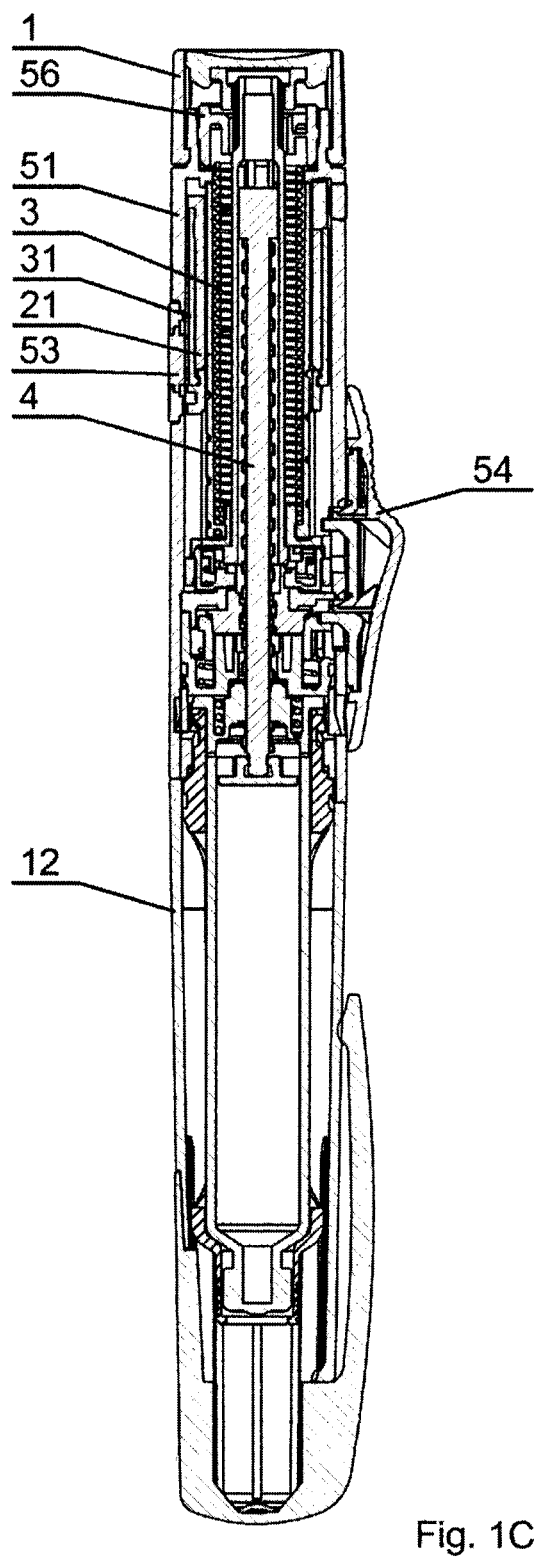
Figure 1D:
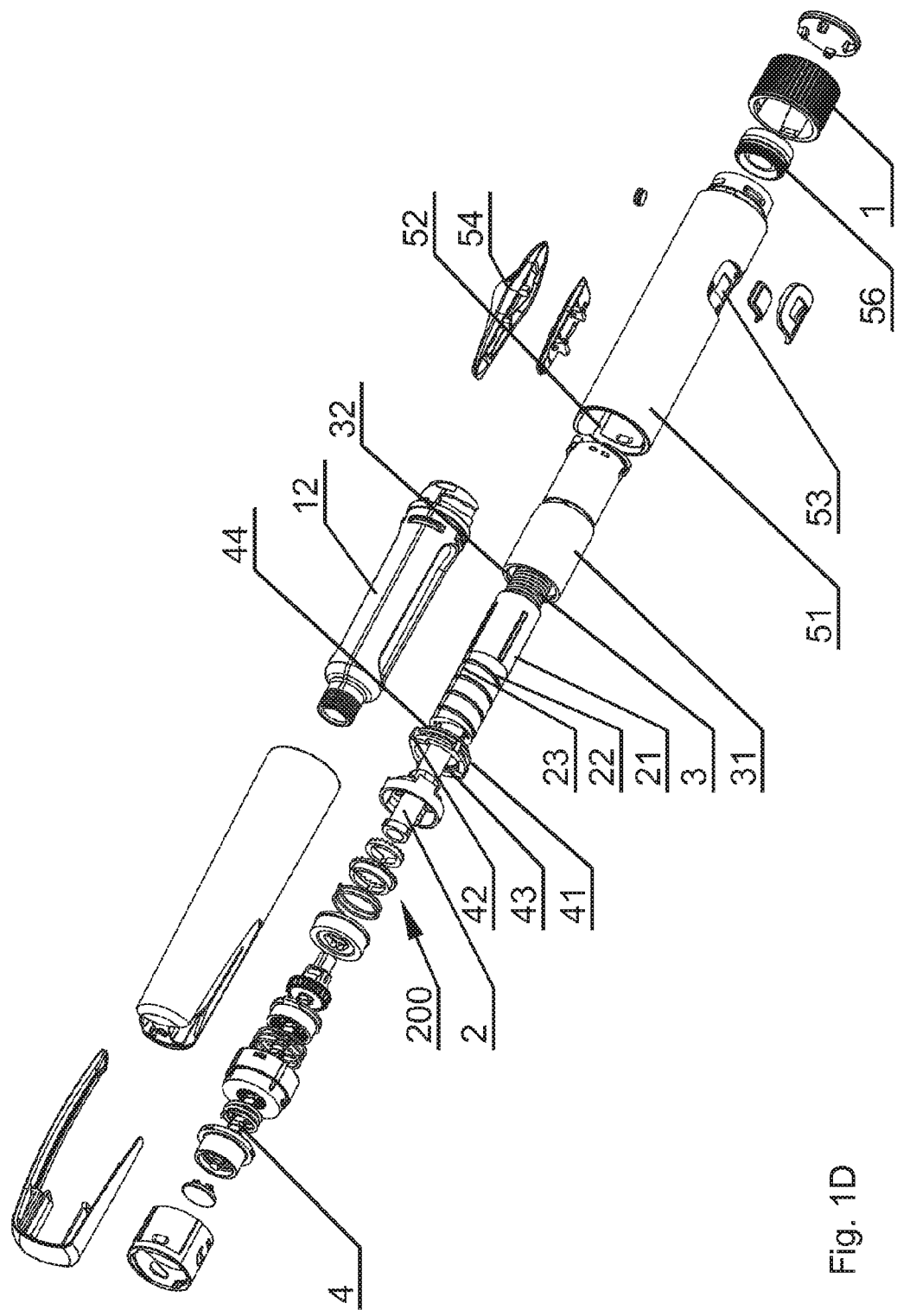

FIGS. 1C, 1D show an example of application of the mechanism in another automatic applicator for liquid pharmaceutical preparations, for example for insulin, for repeated injection delivering of set doses from an exchangeable container. FIG. 1C shows an applicator in a longitudinal cross-sectional view, and FIG. 1D—in an exploded view. An applicator of this type is disclosed in the patent document PL214940 and has a similar principle of operation.

The applicator may comprise an assembly of a least two sleeves connected movably with each other: an indicating sleeve 31 (which can be divided to an inner and an outer part, or which can be integrated) and a driving sleeve 21. The indicating sleeve 31 may comprise indications on its outer surface (not shown in the drawings). The sleeve can be connected longitudinally with a pulling-pushing controlling nut 41. The whole mechanism can be placed in a housing 51. The indicating sleeve 31 can be mounted slidingly, lengthwise and co-axially on the driving sleeve 21 by means of a spline coupling in a form of multi-protrusions comprised of keyways 23 of the driving sleeve 21 and protrusions (not shown in the drawing) of the indicating sleeve 31, wherein the protrusions can be in a form of bayonet protrusions. The indicating sleeve 31 can be mounted slidably between two end positions determining the working range of the indicating sleeve 31. The driving sleeve 21 can be mounted rotatably. The pulling-pushing controlling nut 41 can be mounted on the driving sleeve 21 rotatably by means of threaded connection comprised of a thread groove 22 of the driving sleeve 21 and an internal thread 43 of the controlling nut 41, preferably of non-self-locking threading. The pulling-pushing controlling nut 41 can be mounted in the housing 51 of the applicator slidably longitudinally axially by means of a recess connection, preferably by means of multi-protrusions comprised of the keyways 52 of the housing 51 and protrusions 42 of the pulling-pushing controlling nut 41. The indicating sleeve 31 can be connected longitudinally with the pulling-pushing controlling nut by means of a latch, preferably a circumferential latch comprised of a latch 32 of the indicating sleeve 31 and a latch 44 of the controlling nut 41. The indicating sleeve 31 can be mounted on the driving sleeve 21 with its outer surface located at a set distance with respect to the inner surface of the housing 51 of the applicator, wherein the housing 51 may comprise a window of an inspection opening 53. Indications on the outer surface of the indicating sleeve 31 can be preferably in a form of indicating digits applied spirally. The driving sleeve 21 can be connected with the driving element in a form of spring means, preferably in a form of a cylindrical coil spring 3. The mounting of the spring can be effected by means of bent fragments of distal and proximal parts of the spring (e.g. U-shaped, C-shaped), attached to openings in contact elements (not shown). The spring can also be mounted on a protrusion or indentation, pushed in or permanently melted with the material of the resisting element.

The driving sleeve 21 can be connected with the medicament dosing mechanism in a form of an assembly encompassing a dose setting element (knob) 1, a connecting element 2 of the knob 1 with a setting mechanism, a spring element 3, a lock of the spring element 56, a piston rod 4, a setting mechanism, releasing means (an actuating member) 54 and a housing of a container 12. The dose setting element essentially undergoes a rotatable motion. The releasing elements (or means) can be connected with the spring (driving) element (or means), including in a form a trigger, activating button or other forms (such for example those known from documents WO2009105909, EP2451508, WO2015071289). The releasing means essentially move in the axis of the injector. The releasing means may comprise an additional spring element, which allows returning to the initial position.

The setting mechanism can be a setting mechanism according to at least one of the embodiments as presented herein. In this example of the applicator there is used the setting mechanism 200 equivalent to the mechanism shown in FIGS. 4C-4D (equivalent also to the one shown in FIGS. 2C-2D).

The indicating assembly operates as follows. When the dose is to be set, the driving sleeve 21 should be rotated clockwise (increasing setting) or counter-clockwise (correcting setting). The pulling-pushing controlling nut 41 moves along the driving sleeve and through a threaded coupling by means of the internal thread 43 sliding in a thread groove 22 cut on the outer surface of the cylindrical driving sleeve 21. The rotation occurs with use of the knob 1, wherein after finished injection the knob 1 can take any angular position with respect to the housing during movement opposite to setting movement. This movement can be blocked on the knob, the housing or other elements of the mechanism, including through addition of further element or elements. The pulling-pushing controlling nut 41 can be secured against the rotation by means of the protrusions 42, which slide axially with respect to the keyways 52 produced on the inner wall of the cylindrical housing 51. Such connection allows to retain increased play between the outer cylinder of the pulling-pushing controlling nut 41 and inner cylindrical wall of the housing 51, as well as between outer cylindrical part of the indicating sleeve 31 and inner cylindrical wall of the housing 51, contributing to elimination of friction between cylindrical parts, which is much lower in case of axial friction of the protrusions 42 in the keyways 52 holding the indicating mechanism in central point of rotation. The pulling-pushing controlling nut 41, sliding along the housing 51 pulls during dose setting or pushes conversely during dose correcting the indicating sleeve 31 by means of the protrusions 42 connected rotationally with the latch 32 of the indicating sleeve 31. The indicating sleeve 31 performs a composite motion, because it can be pulled or pushed axially by the controlling nut 41 and at the same time rotates together with the driving sleeve 21, because it can be coupled with it by means of the spline coupling 23 on the outside wall of the cylindrical driving sleeve 21. Such connection allows to retain increased play between the outer cylinder of the driving sleeve 21 and the inner cylindrical wall of the indicating sleeve 31, contributing to elimination of friction between cylindrical parts, which is much lower in case of axial friction of the spline coupling 23 holding the mechanism in the central point of rotation. The composite motion of the indicating sleeve is a spiral motion with respect to the window of the inspection opening 53 in the housing 51, allowing for moving by an arbitrary amount of rotations the indicating sleeve 31 with respect to the housing 51 in a range of axial movement of the indicating sleeve 31 with respect to the driving sleeve 21.

It should be noted that the direction of rotation can be changed so that the increasing setting can be achieved during rotating the driving sleeve 21 anti-clockwise. In such configuration the decreasing setting can be achieved during rotating the driving sleeve 21 clockwise.

The structure of the presented indicating mechanism is based on the principle of cooperating cylinders connected by the spline coupling so that there is essentially no friction between surfaces of cylindrical elements, and consequently the forces coming from other spring (driving) elements can be smaller, which causes a more steady operation of the applicator during dose setting and during delivering the medicament. Axial configuration of the cooperating elements, ensured by multi-protrusions influences the precision of delivering of medicament by eliminating oblique forces acting on dosing elements during dose setting, what influences outdropping of the liquid preparation and decreasing thereby actually provided liquid preparation dose to the one set in the dose setting (selection) phase.

A coupling of indicating elements of the automatic applicator occurs—the indicating sleeve 31 cooperates with the driving sleeve 21. The pulling-pushing controlling nut 41 cooperates with these elements. This allows a precise, controlled decreasing of a mistakenly set excessive medicament dose while maintaining the automatic, stress-less application of the medicament, thereby providing a long-term use when used in an automatic liquid preparation applicator, in particular insulin, in particular for multiple injection delivering of set liquid preparation doses from a container.

Embodiment

Figure 2A:
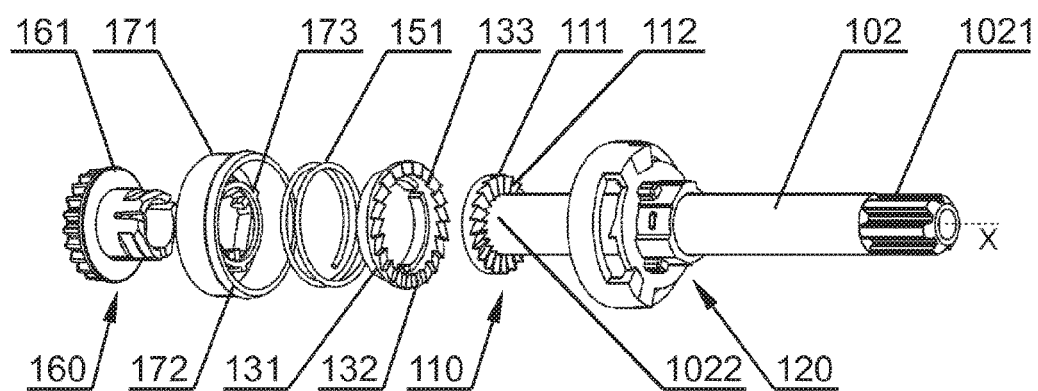
FIGS. 2A-2D show a construction of a mechanism according to one embodiment.
Figure 2B:
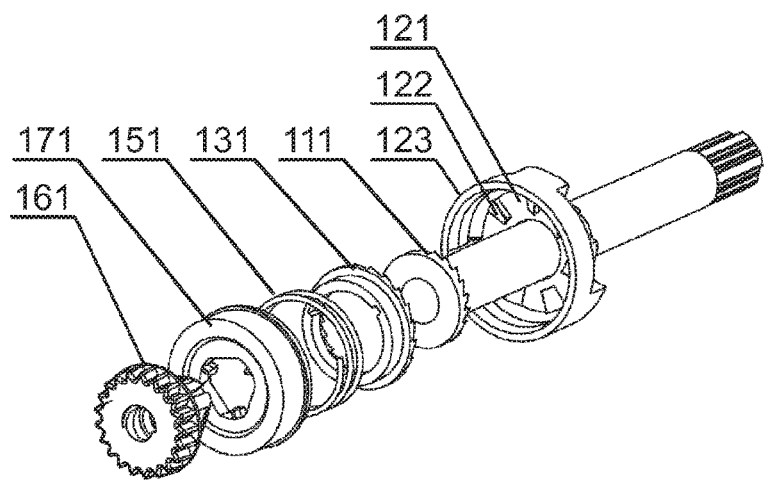

FIGS. 2A, 2B show one of the embodiments of the mechanism in an exploded view, and FIGS. 3A-3D show its method of operation.

The mechanism may comprise a first coupling element. In this example it can be a first movable element, preferably rotatable, preferably a coupling disc 111, which can be coaxial with a main axis X of the mechanism. The first coupling disc 111 can be connected with a dose setting element, for example in a form of a knob (not shown in this drawing). The dose setting element can be connected with the mechanism through a connecting element 102 to transfer the force from user to the mechanism. The connecting element 102 can be for example a rod, a sleeve, a cylinder or other, suitably shaped element. This connection can be provided by the end portion of the connecting element, in this example a first end portion 1021 of the rod 102. On a second end portion 1022 of the rod 102 there can be the first coupling element, in this example the first coupling disc 111. The elements 102 and 111 can be detachable or integrated. The rod 102 and the first coupling disc 111 therefore form the elements of the controlling assembly 110. The controlling assembly 110 can be connected with the dose setting element, by means of which the user can set or correct the dose to be applied. The elements can be connected by inlets, protrusions or other means providing secure mounting.

The mechanism may further comprise a second coupling element. It can be a second coupling disc 121, which can be coaxial with the main axis X of the mechanism. The second coupling disc 121 can be coupled with the first coupling disc 111. In this example, corrugated elements can be providing cooperation between the discs 121 and 111, preferably in a form of teeth 122 of the second coupling disc 121 pointed in the opposite direction to teeth 112 of the first coupling disc 111 and engaged with them. The second coupling disc 121 can be an element of the driving assembly 120, which can be connected with the driving spring (not shown in this drawing) for delivering the dose. The driving spring can be connected with the driving assembly 120 directly or through additional connecting elements.

The mechanism may also comprise a third coupling element. It can be a third coupling disc 131, which can be coaxial with the main axis X of the mechanism. The third coupling disc 131 can be coupled with the second coupling disc 121. In this example, corrugated elements can be providing cooperation between the discs 131 and 121, preferably teeth 132 of the third coupling disc 131 pointed in the opposite direction to the teeth 122 of the second coupling disc 121 and engaged with them. In other words, the third coupling disc 131 may have the teeth 132 pointed in the same direction that teeth 112 of the first coupling disc 111. The third coupling disc 131 can be slidable axially along the main axis X of the mechanism.

A locking element 171 can be connected with the driving assembly 120. This connection may be provided by a latch 172 connected with a latch 123 or other connecting means. The locking element 171 immobilizes in a rotary manner the third coupling disc 131 with respect to the locking element 171. Moreover, the locking element 171 allows an axial movement for the third coupling disc 131 with respect to the locking element 171. For example, protrusions 173 coupled slidably with inlets 133 in the third coupling disc 131 can be provided for this purpose.

To the locking element 171 there can be connected, directly or through additional elements, a nut 161, which can be adapted for rotating the piston rod for dosing the set dose (not shown in this drawing). The nut 161 may therefore be an element of the dosing assembly 160 of the mechanism.

Between the third coupling disc 131 and the locking element 171 there can be mounted a pressing element for pressing the third coupling disc 131 towards the second coupling disc 121. In this example the pressing element can be a pressing spring 151, but the pressing element can also be a spring element of another type, constituting a separate element or an integral part of at least one of additional elements. For example, these can be a resilient protrusions formed in the third coupling disc 131 or the locking element 171.

In this embodiment, the controlling coupling 110 can be therefore coupled with the dosing assembly 160 by the spring element 151, which during the rotation of the dose setting knob deforms to a decoupled position and allows movement of the controlling assembly 110 with respect to the dosing assembly 160, and in a coupled position blocks rotation of the controlling assembly 110 with respect to the dosing assembly 160.

In other words, in this embodiment the setting mechanism may comprise at least four rotatable elements connected with each other (102, 111, 121, 131, 151, 160, 171), wherein at least two of them (102, 111, 121) can be rotatable during setting or reducing of the dose for the dosing device. The first rotatable element (111) can be a receiving element and may comprise corrugations, and the second rotatable element (121) may comprise corrugations cooperating with the corrugations of the first rotatable element, wherein said corrugations can be shaped so that they allow rotation of said at least four (102, 111, 121, 131, 151, 160, 171) rotatable elements during delivering of the dose by the dosing device.

The mechanism according to this embodiment operates as follows.

During setting or correcting of the dose, the mechanism can be blocked motionless with respect to the casing of the applicator, for example the knob 161 can be maintained motionless with respect the casing of the applicator (by means of the lock or releasing means, for example by means of an actuating member). When a dose is to be applied, the knob 161 should be released and the whole mechanism rotates simultaneously by means of the driving spring for delivering the dose, and its elements maintain the same position with respect to each other. Therefore the mechanism operates when the dose is set or reduced (corrected).

Figure 3A:
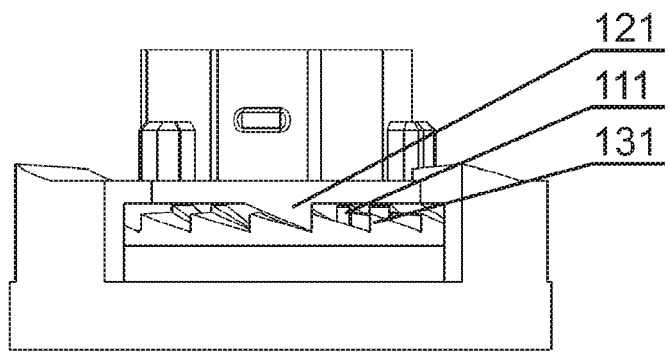
FIGS. 3A-3D show its method of operation.

The initial position is shown in FIG. 3A.

Figure 3B:
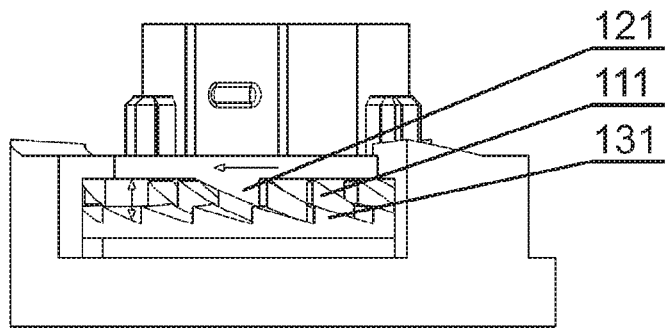

During dose setting, which is shown in FIG. 3B, when the user starts rotating the first coupling disc 111 using a knob in the dose setting direction, indicated with horizontal arrow, it causes a rotation of the second coupling disc 121, because the coupling discs 111 and 121 can be meshed with each other. Because the third coupling disc 131 cannot rotate, it starts sliding on the inclined walls of the teeth and at the same time it moves downwards, tensioning the spring 151. This element moves axially. This is happening until the tips of the teeth of the second coupling disc 121 and the third coupling disc 131 pass each other, and then the spring 151 presses the disc 131 back to the initial position, but one tooth further.

The rotating coupling disc 121 tensions the driving spring, accumulating thereby in it a force for expelling the dose.

Figure 3C:
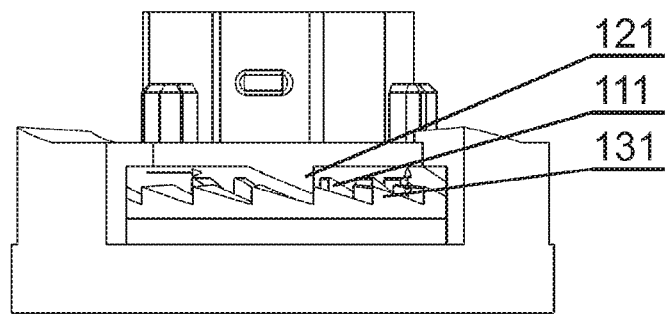
Figure 3D:
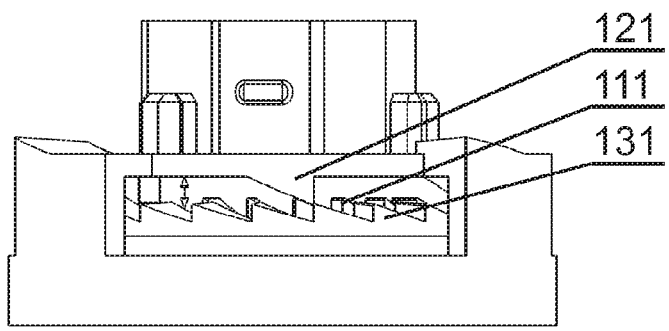

During dose correcting, which is shown in FIG. 3C, when the user starts rotating the first coupling disc 111 using the knob in the dose correcting direction, opposite to the dose setting direction, indicated by the horizontal line, the teeth 112 of the first coupling disc 111 start to slide with respect to the teeth 122 of the second coupling disc 121, which causes a downward movement of the first coupling disc 111, accompanied with the third coupling disc 131 and compression of the spring 151.

The distance between the discs: the second one 121 and the first one 111 and the third one 131 increases until the moment, when the tips of the teeth of the second disc 121 do not pass the tips of the teeth of the third disc 131. It is important that the teeth 132 of the third disc 131 were not higher than the teeth 112 of the first disc 111 and thus would not cause decoupling of the first disc 111 and the second disc 121, as it can be seen from FIG. 3D.

When the tips of the teeth of the second disc 121 and the third disc 131 pass each other, then the second disc 121 can be released from coupling with the third disc 131 and due to the action of the driving spring it starts to rotate, releasing thereby the energy accumulated in the driving spring. At the same time, the spring 151 causes an axial return movement of the first disc 111 and the third disc 131 towards the second disc 121 and the whole mechanism can be corrected by one dose.

Therefore, both during dose setting and correcting, the third coupling disc 131 does not rotate. The third coupling disc 131 rotates however during dose delivering, when it is rotated together with the nut 161. The rotation of the second disc 121 with respect to the third disc 131 defines a degree of spring tension and the dose to be applied.

Figure 2C:
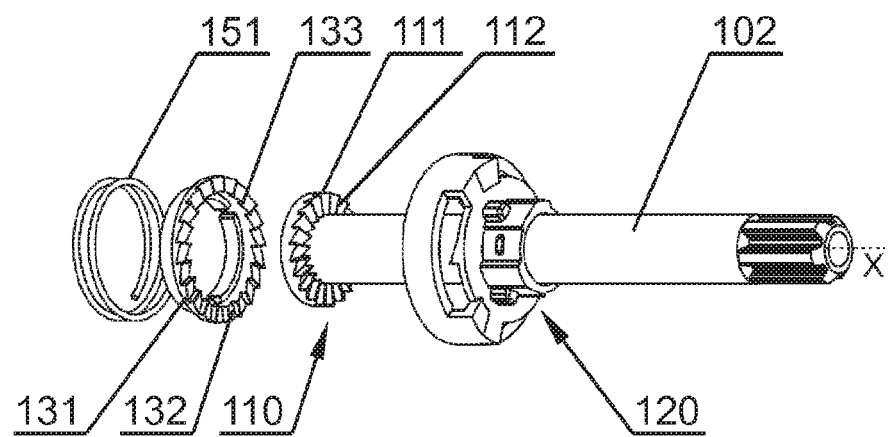
Figure 2D:
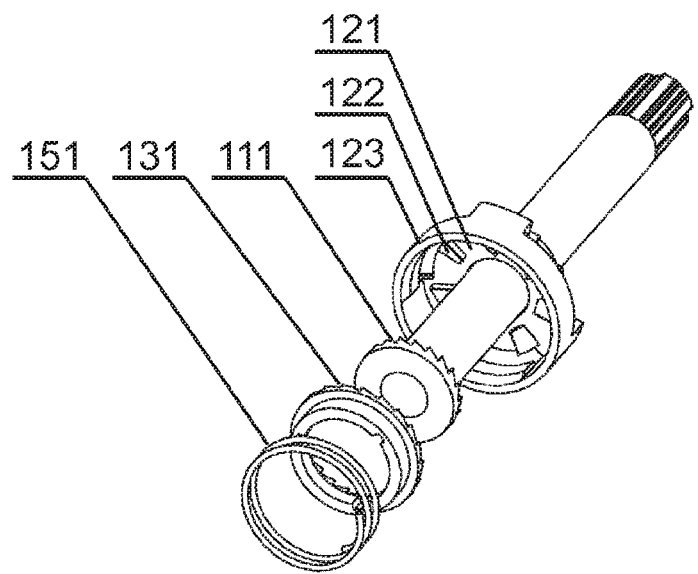

FIGS. 2C and 2D show an embodiment of the setting mechanism, the elements of which can be analogous to the example of FIGS. 2A-2B, whereas the elements not shown may have other forms. The mechanism shown in FIGS. 2C and 2D resembles a clutch. The spring element 151 can be supported on other kinds of elements than those shown in the example of FIGS. 2A-2B, for example the housing of the device, an element of other mechanism etc.

Embodiment

Figure 4A:
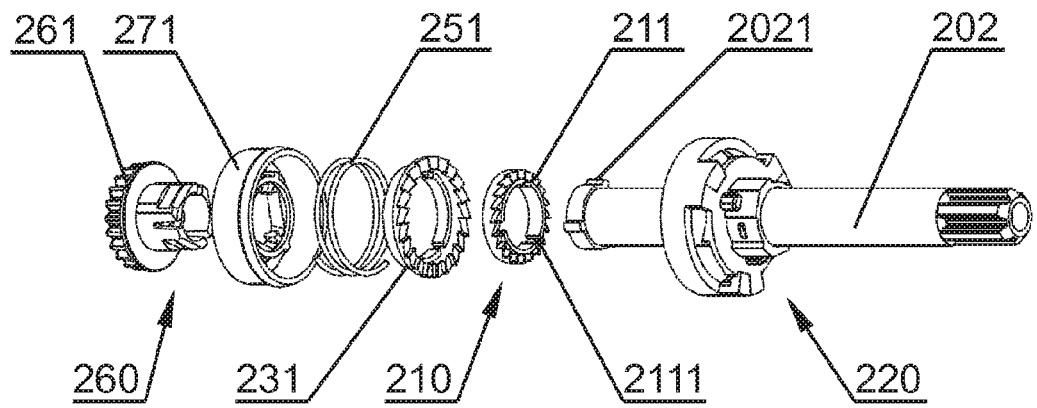
FIGS. 4A-4D show a construction of a mechanism according to another embodiment.
Figure 4B:
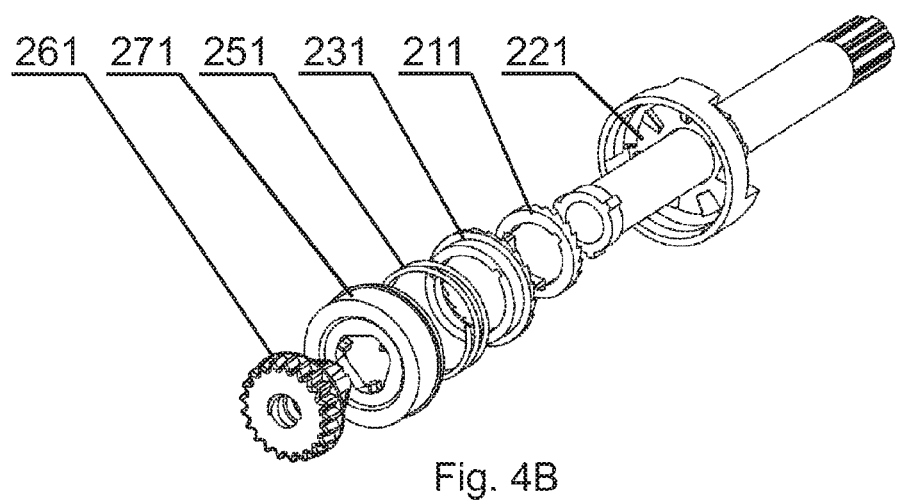

FIGS. 4A-4B show another embodiment of the setting mechanism.

The mechanism differs from the embodiment of FIGS. 2x and 3x in that the rod 202 and the first coupling disc 211 can be elements movable axially with respect to each other. In this example the first coupling disc 211 may have a form of a ring with inlets 2111 formed inside in its inside band, which cooperate with longitudinal protrusions 2021 formed on the end of the rod 202.

Consequently, when the first coupling disc 211 moves axially during operation of the mechanism, the rod 202 can retain its axial position, which contributes to simplification of the mechanism in part encompassing the rod 202, and especially its connection with the dose setting and/or correcting element.

The remaining elements of this embodiment, denoted with reference signs 2xx, can be equivalent to elements of the embodiment shown in FIGS. 2x and 3x and denoted with reference signs 1xx.

Figure 4C:
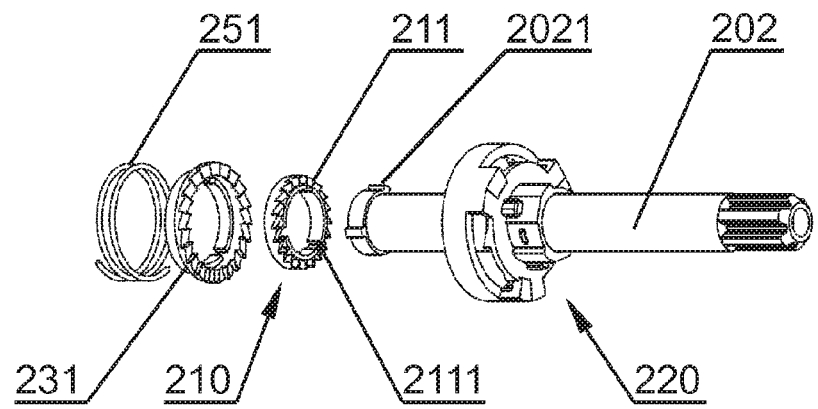
Figure 4D:
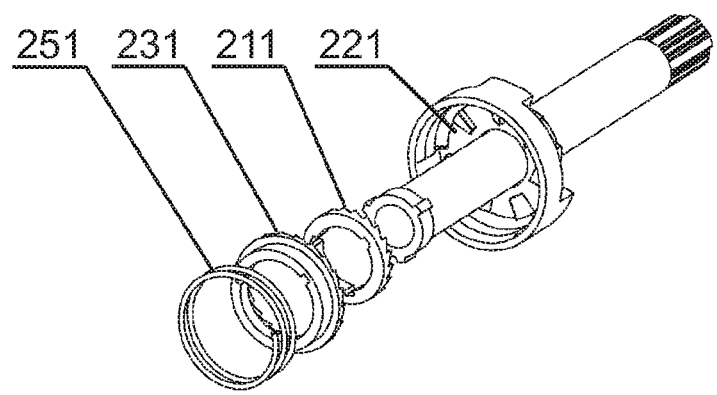

FIGS. 4C and 4D show a setting mechanism, the elements of which can be analogous to the example of FIGS. 4A-4B, wherein the elements not shown may have other forms. The mechanism shown in FIGS. 4C and 4D is a claw clutch. In this mechanism the clutch moves axially. The spring element 251 can be supported on other elements than those shown in FIGS. 4A-4B, for example housing of the device, an element of another mechanism etc. The shown rotatable elements can be configured so as to define substantially an equal force acting both in the dose setting direction and in the opposite direction. Deviations in this range can result from technological specification of the produced device, e.g. manufacturing tolerances of components. Nevertheless, the operation principle of the device should ensure substantially same (equal) force (taking into account possible manufacturing deviations).

In another embodiment the mechanism can be used to separate set substance doses in the dosing device in connection with claw clutch. The dosing device may comprise a coupling element, in a form of a nut or a ring with the possibility of moving to the selected set position, connected functionally with the mechanism. Movement of the dose setting element in the first dose setting direction can be accompanied by tensioning the driving spring, which provides a force for expelling the set dose. The device may comprise means for releasing the nut, which causes returning of the mechanism to its initial position for driving the rod through unidirectional coupling, in order to expel the set dose. The device may comprise an assembly of a screw with threading of big (fast) pitch, capable of transforming the rotary motion of the mechanism to a linear movement of the piston rod. The movement of the piston rod can be achieved by using the energy stored in the driving element, which preferably can be twisted when the initially set substance dose for injecting can be set through a movement of the dose setting element in the first direction. Preferably, the dose setting element can be a knob, performing a rotary movement, positioned substantially in the end part of the injector. The piston rod may comprise a non-circular cross-section and an outer thread. A drive of the piston rod may comprise two elements, that can be a piston rod guide and a nut, which may have an inner thread matching the thread of the piston rod. Between the nut and the piston rod guide there can be a unidirectional coupling, allowing for rotation of these parts in one direction, but not in the opposite direction, wherein the rotation, which was made possible is the only one, by which the piston rod is carried in a circumferential direction in the device. The coupling can be designed so that the initial resistance, large enough to resist the torque acting on the coupling due to setting of the dose, should be overcome for a rotation to occur. In the nut, instead of the thread, there can be present a guiding track. In such case, the piston will both rotate and move axially (during the injection).

Embodiment

Figure 5A:
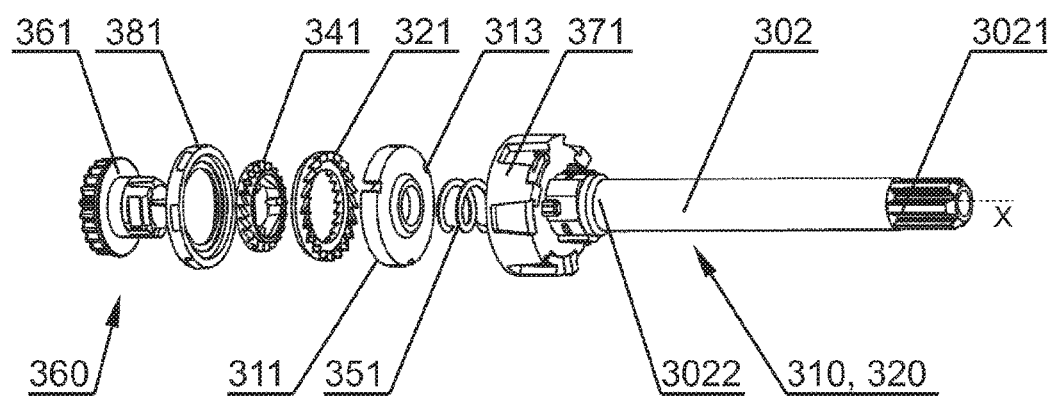
FIGS. 5A, 5B show another embodiment of a mechanism.
Figure 5B:
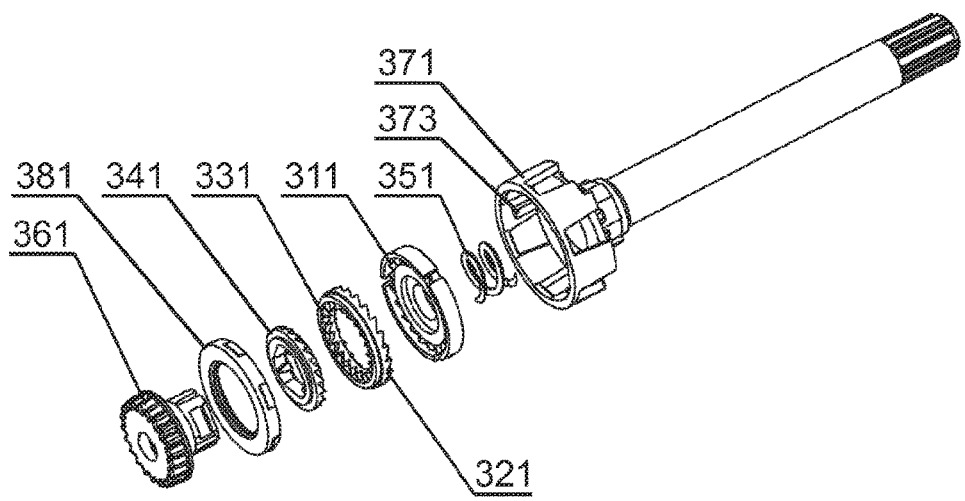
Figure 5C:
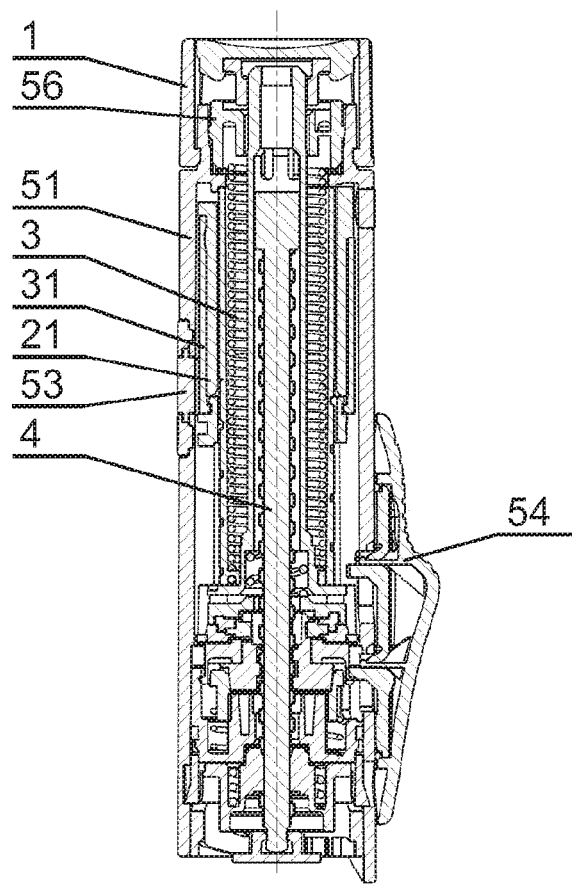
FIGS. 5C, 5D show an example of an applicator, wherein this mechanism can be used.
Figure 5D:
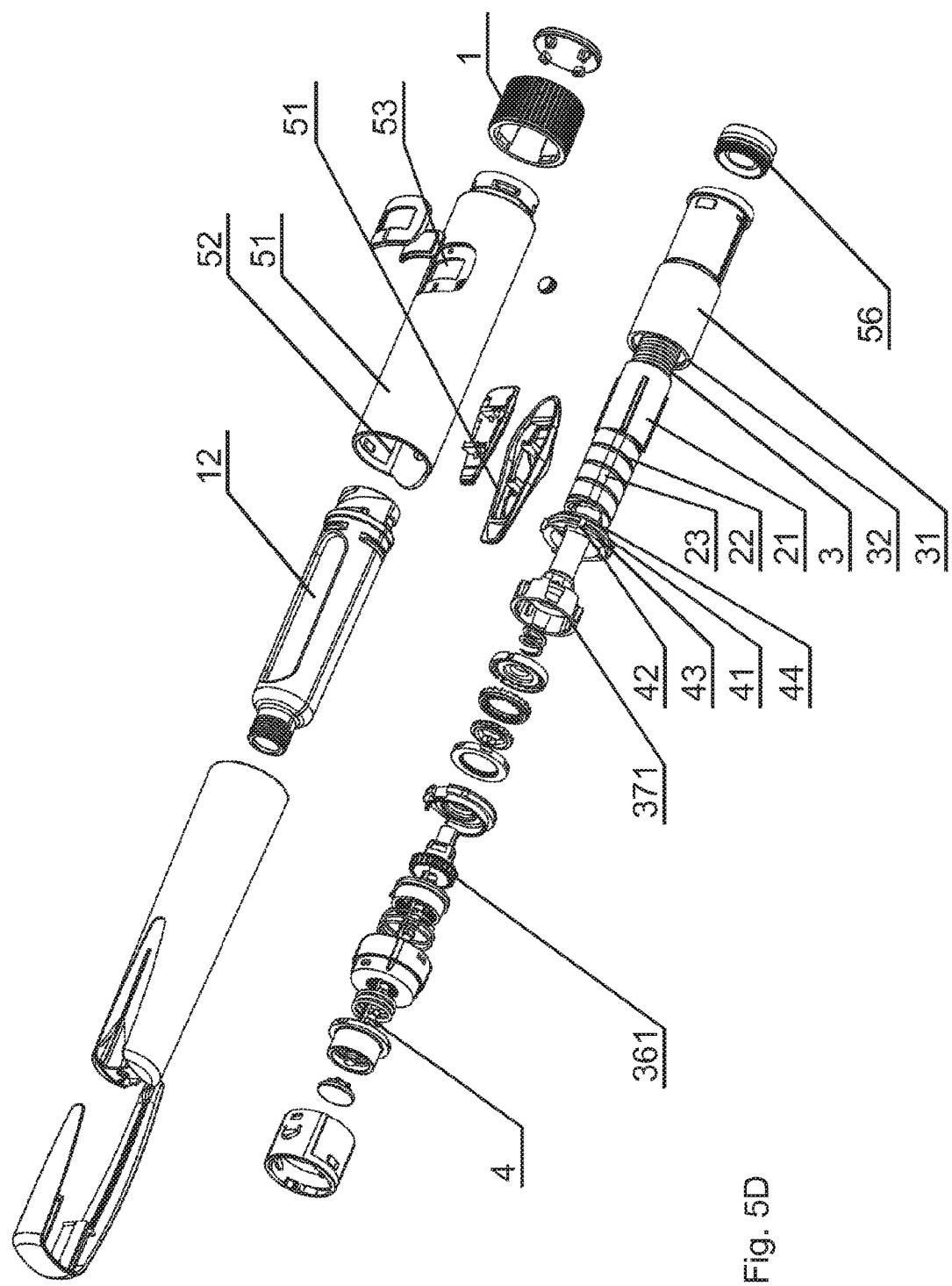

FIGS. 5A, 5B show another embodiment of the mechanism in an exploded view, FIGS. 5C, 5D show an example of applicator, wherein this mechanism can be used, and FIGS. 6A-6D show its method of operation in a view in a partial cross-section.

The mechanism may comprise a first coupling element. In this case, it can be a first coupling disc 311, which can be coaxial with the main axis X of the mechanism. The first coupling disc 311 can be rotated by a dose setting element, for example in a form of a knob (not shown in this drawing). The element connecting the first coupling disc 311 with the dose setting element can be a connecting element 302, which can be for example a rod, a sleeve, a cylinder or other suitably shaped element. This connection can be allowed by an end part of the connecting element, for example a first end part 3021 of the rod 302. On the other end part 3022 of the rod 302 there can be a housing 371 (which can also be named as a clutch). The housing 371, the rod 302 and the first coupling disc 311 can be the elements of the controlling assembly 310. It can be connected with the dose setting element, by means of which the user can set or correct the dose to be applied.

The housing 371 can be further connected with a driving spring (not shown in this drawing) for delivering the dose, thus in this embodiment the housing 371 can be also an element of the driving assembly 320. The driving spring can be thus connected to both controlling assembly 310 and the driving assembly 320. The driving spring can be connected with the housing 371 directly or through additional connecting elements. The first coupling disc 311 can be movable axially along the main axis X of the mechanism. In this embodiment the first coupling disc 311 may have on its outer rim inlets 313, which cooperate with the longitudinal protrusions 373 on the inner surface of the cylindrical housing 371.

The mechanism may comprise further a second coupling element. In this example it can be a second coupling disc 321, which can be coaxial with the main axis X of the mechanism. The second coupling disc 321 can be coupled with the first coupling disc 311. In this example the element providing cooperation between the first disc 311 and the second disc 321 can be teeth 322 of the second coupling disc 321 pointed in the opposite direction than teeth 312 of the first coupling disc 311 and can be engaged with them. In this case the second coupling disc 321 can be movable axially along main axis X of the mechanism. The second coupling disc 321 can be movable with the first coupling disc 311.

The mechanism may also comprise a third coupling element. In this embodiment it can be a third coupling disc 331, which can be coaxial with a main axis X of the mechanism and can be mounted on the other side of the ring, on which the second coupling disc 321 can be situated. In other examples, the second disc 321 and the third disc 331 can be situated on different elements. The third coupling disc 331 can be movable axially along main axis X of the mechanism.

The housing 371 together with a stopping ring 381 form the elements of the locking assembly, inside which the coupling discs move, wherein the first coupling disc 311 can be only movable axially with respect to the locking assembly, and the other discs can be movable axially and can be rotatable with respect to the locking assembly.

In the locking assembly there can be also a nut 361, which can be configured for rotating the piston rod for dosing the dose (not shown in the drawing). The nut 361 thus forms an element of the dosing assembly 360 of the mechanism. The nut 361 can be connected with a fourth coupling disc 341, which can be coaxial with the main axis X of the mechanism. The fourth coupling disc 341 can be connected rotatably with the driving assembly 310 through further coupling discs, that can be the third disc 331, the second disc 321 and the first disc 311.

Between the first coupling disc 311 and the housing 371 there can be mounted a pressing element for pressing the first coupling disc 311 towards the second coupling disc 321. In this embodiment, the pressing element can be a compression spring 351, but it can also be another type of spring element, constituting a separate element or an integral component of at least one of the remaining elements. For example, it can be resilient protrusions formed in the first coupling disc 311 or the housing 371 of the controlling assembly.

Thus, the first coupling disc 311 can be connected with the controlling assembly 310 so as to enable axial movement of the first disc 311 with respect to the controlling assembly 310. The controlling assembly 310 can rotate during dose setting, dose correcting and during application of the medicament. The second disc 321 and the third disc 331 can perform both rotary and axial movement. The fourth coupling disc 341 can be connected rigidly to the nut 361. Between the housing 371 and the first toothed disc 311 there can be a compression spring 351 which can be compressed during dose setting and correcting. The stopping ring 381 can be fixedly connected with the housing 371, what causes that spring forces can be contained within this assembly and are not conveyed onto other parts of the applicator.

In other words, in this embodiment the setting mechanism may comprise at least four rotatable elements (302, 311, 321, 331, 341, 351, 361, 371) connected to each other, wherein the rotatable elements (302, 311, 321, 331, 351, 371) can be rotatable during dose setting or dose reducing for the dosing device. The first rotatable element (311) can be a receiving element and may comprise corrugations, and the second rotatable element (321) may comprise corrugations cooperating with corrugations of the first rotatable element, wherein these corrugations can be shaped so that they allow rotation of said at least four rotatable elements (302, 311, 321, 331, 341, 351, 361, 371) during delivering of the dose by the dosing device.

The mechanism according to this example operates as follows.

The mechanism operates using four coupling element comprising corrugated surfaces cooperating with each other, preferably toothed discs.

Figure 6A:
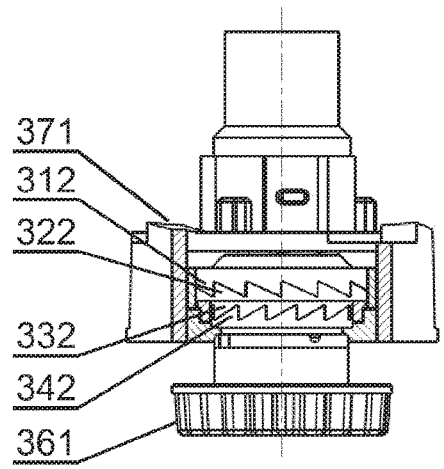
FIGS. 6A-6D show its method of operation in a partial cross-sectional view.
Figure 6B:
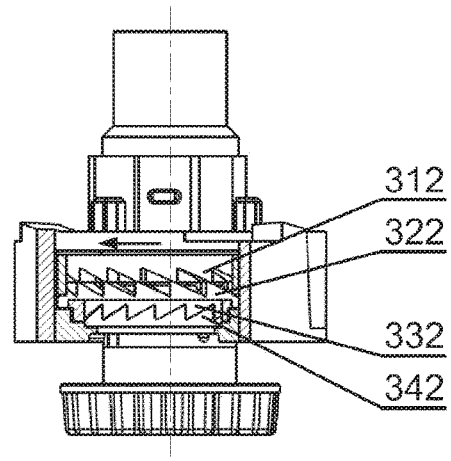

The initial state is shown in FIG. 6A.

Figure 6C:
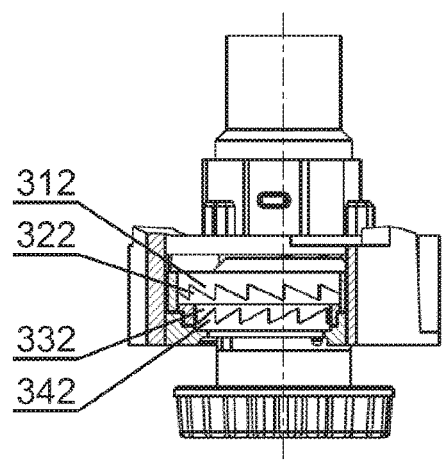

During dose setting, the housing 371 can be the driving element. When the user starts rotating it by means of a knob (in the direction indicated by arrow in FIG. 6B), it causes a simultaneous rotation of the first rotatable disc 311, because the elements 371 and 311 can be connected with the connecting elements 313, 373. Because the first disc 311 cannot rotate with respect to the housing 371 it rotates together with it, and its teeth 312 start sliding on the oblique walls of the teeth 322 of the second toothed disc 321 and at the same time the first disc 311 moves upwards and tensions the spring 351. The second toothed disc 321 can be connected immovably with the third toothed disc 331. The third toothed disc 331 can be engaged with the fourth toothed disc 341. The fourth toothed disc 341 can be connected to the nut 361. Consequently, the movement of the second toothed disc 321 can be impossible. This happens until the tips of the teeth 312 and 322 pass each other and then the spring 351 presses back the first disc 311 to the initial position, but one section further, as shown in FIG. 6C.

Figure 6D:
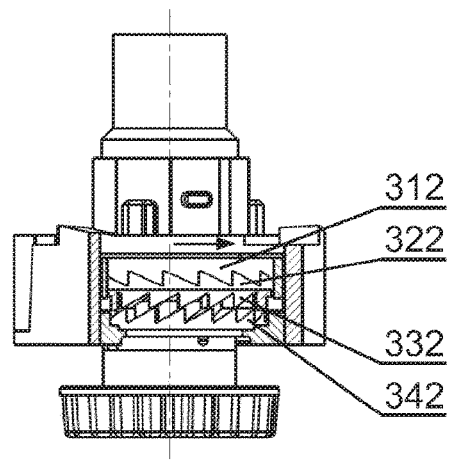

In order to correct the dose, the housing 371 should be rotated in the direction opposite to the dose setting direction (that is in the direction shown by arrow in FIG. 6D). The first coupling disc 311 cannot rotate with respect to the housing 371, so these two elements start rotating. During dose correcting the teeth 312 of the first disc 311 can be thus immovably engaged with the teeth 322 of the second disc 321. The teeth 332 of the third disc 331, connected with the second disc 321, start sliding on the oblique walls of teeth 342 of the fourth disc 341, which causes upward movement of the third disc 331, the second disc 321 and the first disc 311 and tensioning of the spring 351. This happens until the tips of the teeth 332 and 342 between the elements pass each other, and then the spring 351 presses back the element to the initial position, but one section earlier, to the position as shown in FIG. 6A. The design of the setting mechanism, in particular of the rotatable elements, allows achieving their mutual configuration, which defines substantially equal force acting both during movement in the dose setting direction and during movement in the opposite direction. It should however be noted, that depending on manufacturing tolerances of the elements in given device, there can occur noticeable smaller or bigger deviations in this range.

The mechanism can be used in an applicator as discussed in FIGS. 1C, 1D—the elements shown in FIGS. 5C and 5D can be equivalent to the elements shown in FIGS. 1C, 1D.

Embodiment

Figure 7D:
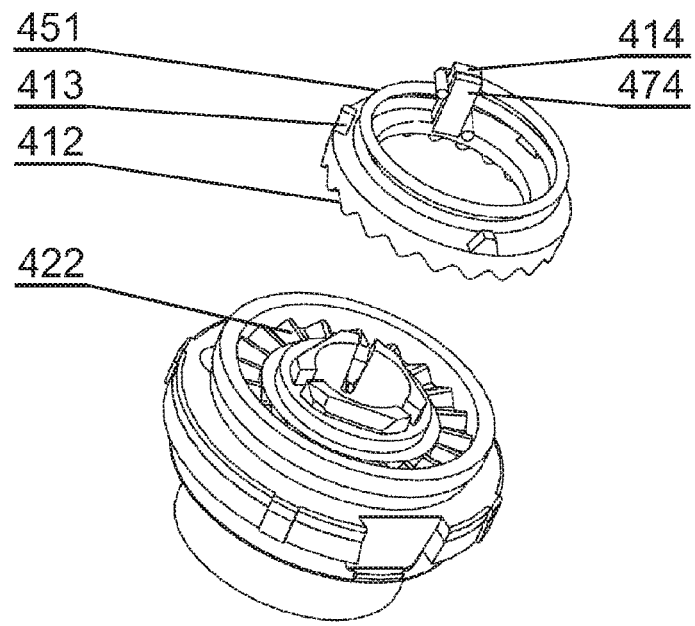
Figure 7E:
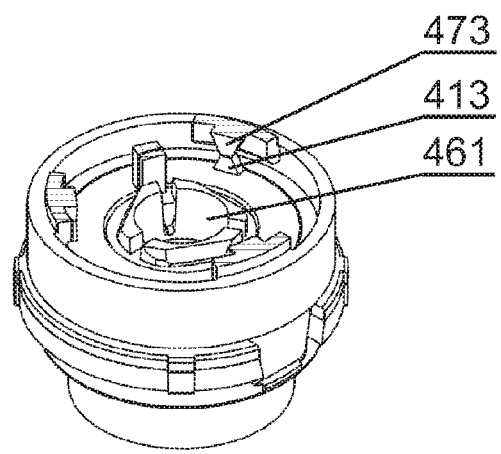
Figure 7F:
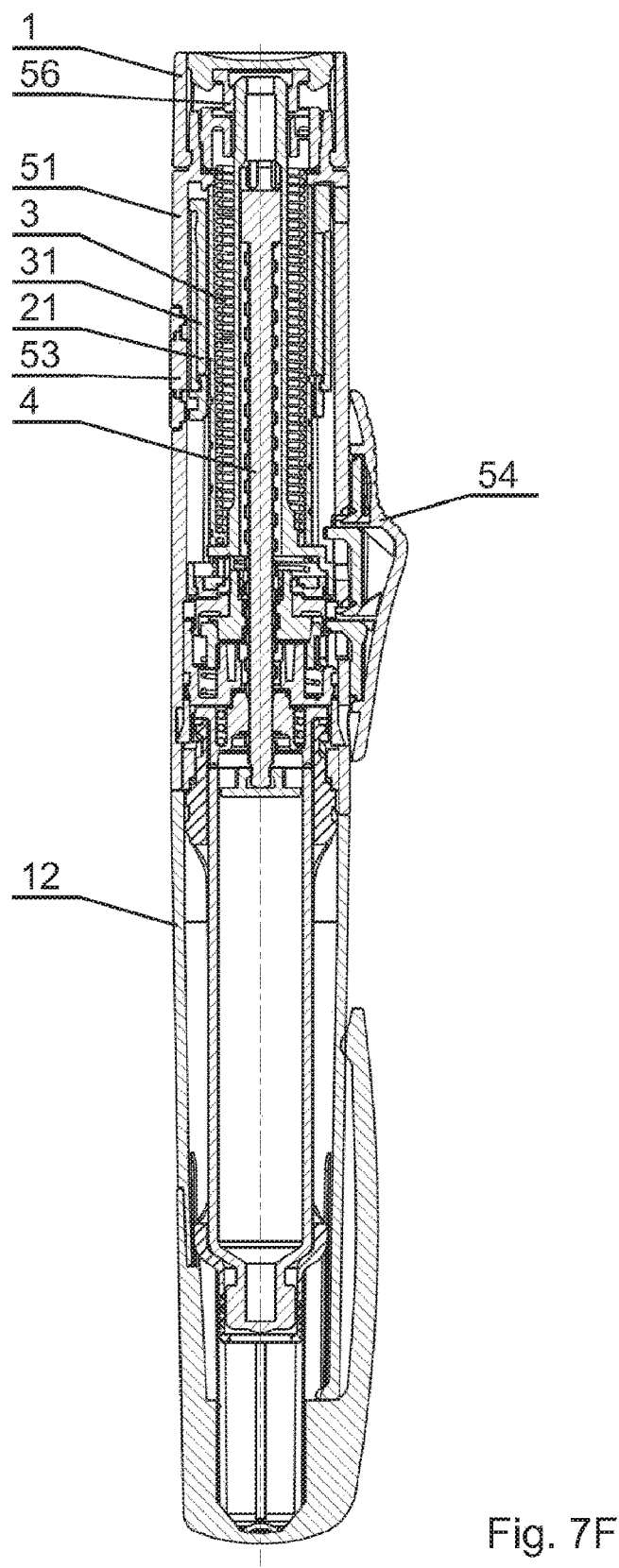
FIGS. 7F-7G show a construction of an example of an applicator, wherein this mechanism can be used.
Figure 7G:
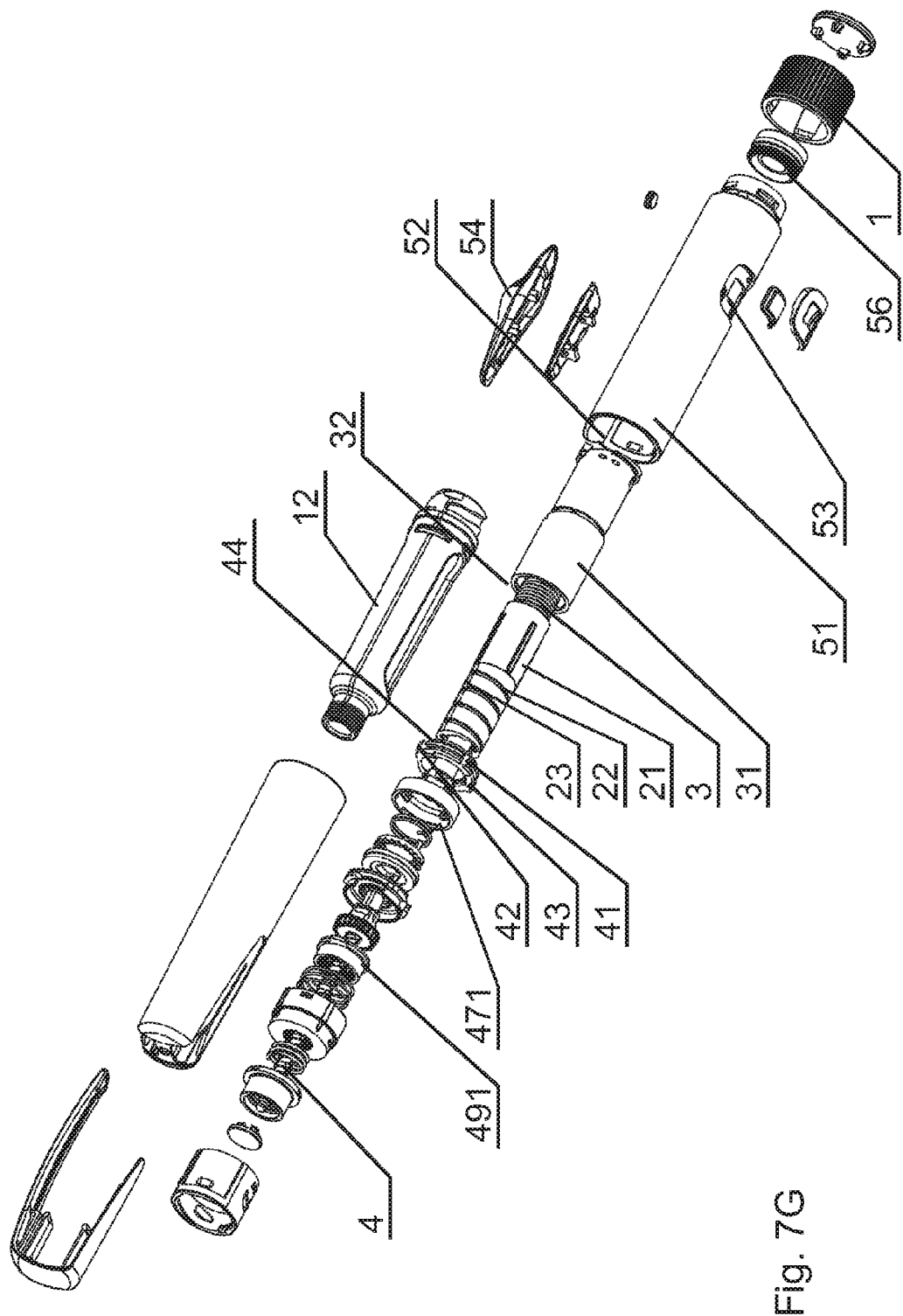

FIGS. 7A-7E show another embodiment of the mechanism, FIGS. 7F-7G show the design of an example of an applicator, wherein this mechanism can be used, and FIGS. 8A-8H show its method of operation.

The mechanism may comprise a housing 471 (which can also be called a clutch) which can be connected, preferably rigidly, with a dose setting element, for example in a form of a knob (not shown in the drawing). A connecting element 402 connects the housing 471 with the dose setting element. The connecting element 402 can be in a form of a rod, a sleeve, a cylinder or other suitably shaped element. The connection can be provided by an end part of the connecting element, in this case a first end part 4021 of the rod 402.

The mechanism may comprise a first coupling element. In this case it can be a first coupling disc 411 (which can be also known as a latch), which can be coaxial with the main axis X of the mechanism. The first disc 411 may have on the side opposite to its teeth 412 a lock 413 in a form of a protrusion, preferably of trapezoid shape or other shape of narrowing legs. For a secure angular position between the first disc 411 and the housing 471, the lock 413 abuts a lock 473 of the housing 471, which also may have preferably a trapezoid shape or another shape of narrowing legs. Preferably, the locks 413, 473 may have a form of plurality of protrusions, for example three protrusions arranged evenly on the circumference of the first disc 411 and of the housing 471. For another angular position relation between the first disc 411 and the housing 471, the lock 413 of the first disc 411 does not abut the lock 473 of the housing 471, what enables axial movement of the first disc 411 towards the housing 471.

Between the first disc 411 and the housing 471 there can be a torsion element, preferably a spring 451, preferably a torsion spring or torsion-compression spring, or an arrangement of an torsion and compression element. The spring 451 may have two end portions 452 and 453 pointed inward, which can be hooked respectively to protrusions 474 of the housing 471 and protrusion 414 of the first disc 411.

The housing 471, the rod 402, the spring 451 and the first coupling disc 411 can be elements of the controlling assembly 410. It can be connected with the dose setting element, by means of which the user can set or correct the dose to be applied.

The mechanism may also comprise a second coupling element. It can be a second coupling disc 421 (which can also be called a latch), which can be coaxial with the main axis X of the mechanism. The second coupling disc 421 can be coupled with the first coupling disc 411. In this example the element providing cooperation between the first disc 411 and the second disc 421 can be teeth 422 of the second coupling disc 421 pointed in the opposite direction than teeth 412 of the first coupling disc 411 and can be engaged with them. Instead of the teeth 412, 422 other corrugated elements can be used. The second coupling disc 421 can be mounted fixed axially with respect to the housing 471 by means of a latch 425 cooperating with a latch 475 of the housing 471.

A nut 461 can be connected in a non-rotary and non-slidable way with the second coupling disc 421, which can be configured to rotate a piston rod 404 for dosing the dose. The nut 461 can be thus an element of the dosing assembly 460 of the mechanism.

During dose setting or correcting, the elements 402, 411, 451, 471 rotate, and others remain motionless. The mechanism can be maintained motionless with respect to the housing of the device by means of an actuating member 491. After releasing the actuating member 491 (as shown in FIG. 8H), the lock of the mechanism can be released and it can rotate by the force accumulated in the driving spring, thereby causing movement of the piston 404 by the thread of the element 461.

A locking element 481 can be mounted in a set position with respect to the applicator's housing and preferably does not rotate during dose setting or correcting or during dosing the dose. It can be preferably a bearing element.

The mechanism according to this embodiment operates as follows.

Figure 8A:
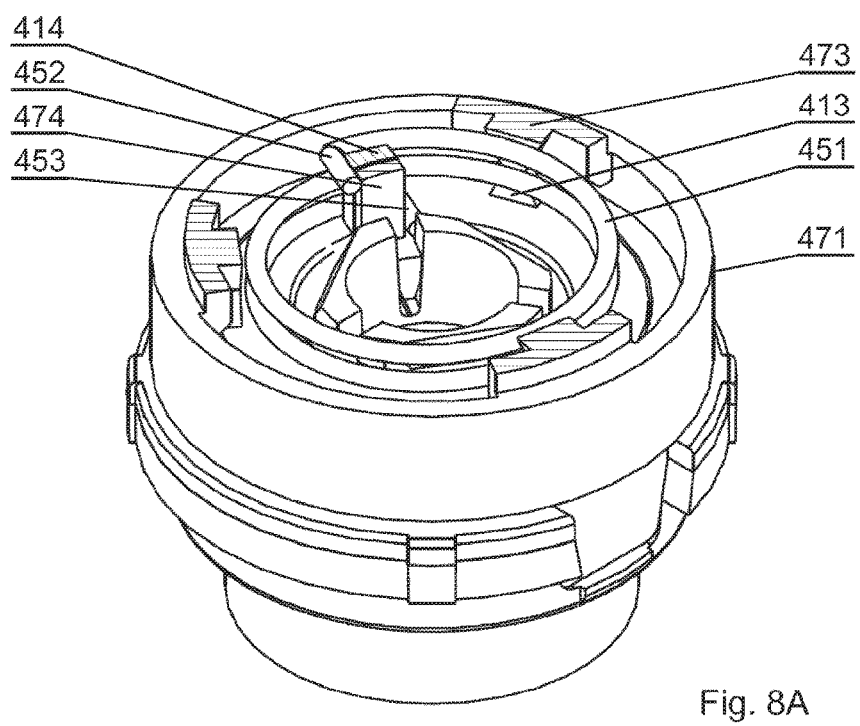
FIGS. 8A-8H show its method of operation.

In the initial position, shown in FIG. 8A, the first coupling disc 411 and the second coupling disc 421 are maintained and blocked in rested state by the lock 473 of the housing 471 and the lock 413 of the first disc 411. The initial tension of the spring 451 causes fixing the position of the first disc 411 with respect to the housing 471.

Figure 8B:
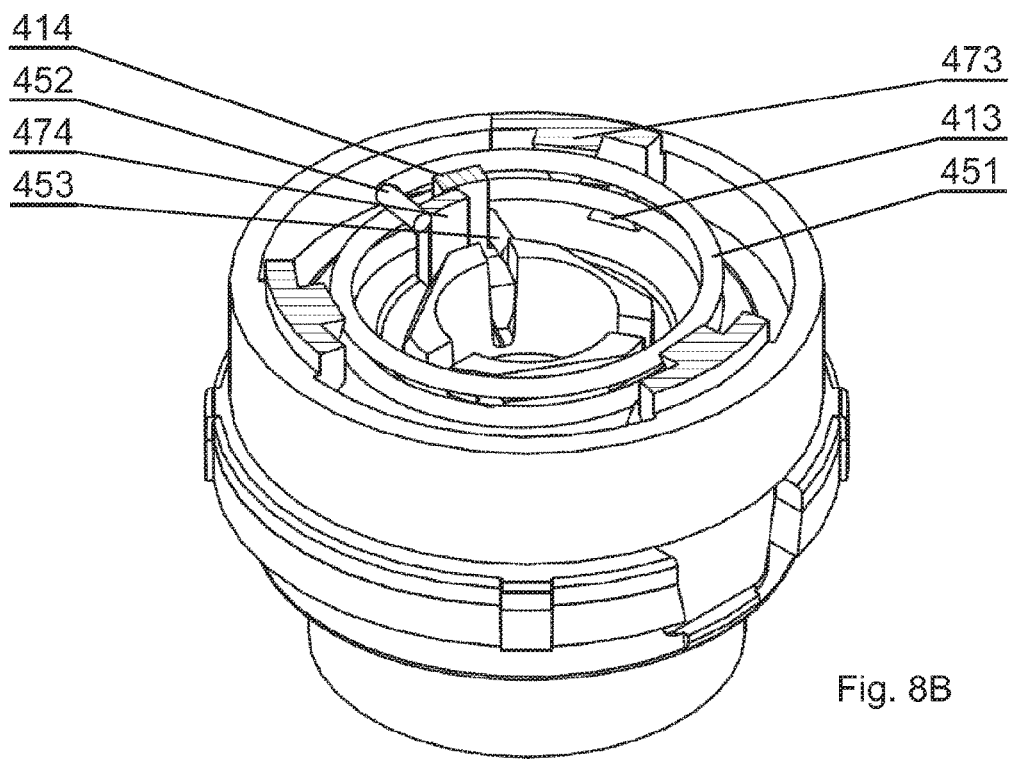

When during dose setting the user rotates the knob, it causes a rotation of the housing 471. This movement causes movement of the housing 471 by a certain angle with respect to the first disc 411, which can be accompanied by tensioning off the spring 451. At the same time, the locks 473 and 413 can be also moved by the same angle and the first disc 411 can be no longer blocked in the axial direction, as shown in FIG. 8B.

Figure 8C:
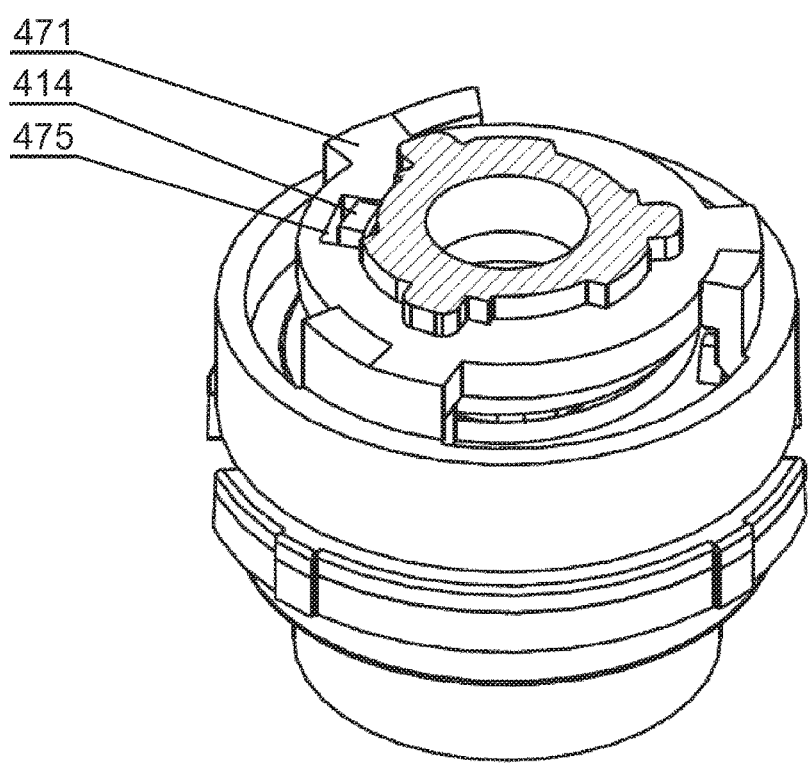

A maximal angle of movement of the housing 471 with respect to the first disc 411 can be predetermined by the protrusion 414, which moves in a recess 475 of the clutch 471. When those elements reach their movement limit, they continue moving together, as shown in FIG. 8C.

Figure 8D:
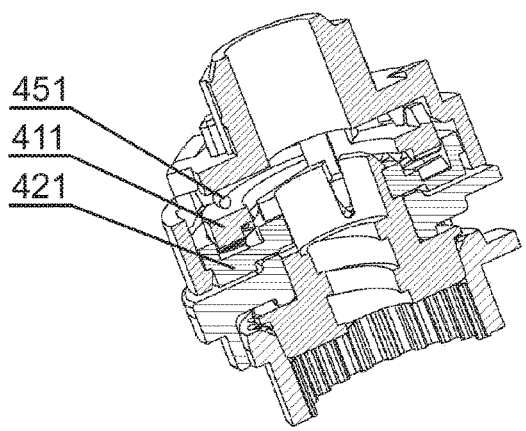
Figure 8E:
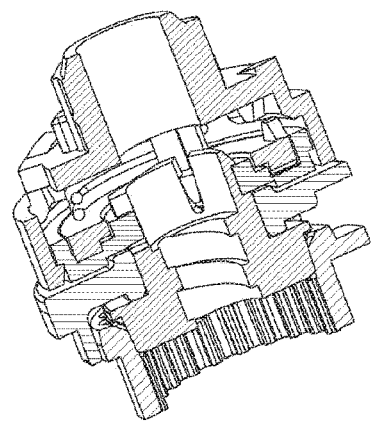

Because the first disc 411 can be unblocked in the axial direction, it moves so that its teeth 412 jump over a subsequent teeth 422 of the second disc 421, assuming subsequent engagement positions. The spring 451 can be here an element flexible in axial direction, which forces the first disc 411 to move as shown in FIG. 8D (first disc 411 is lifted, the spring 451 is compressed) and in FIG. 8E (first disc 411 is pressed to the second disc 421, the spring 451 is loosened).

Figure 8F:
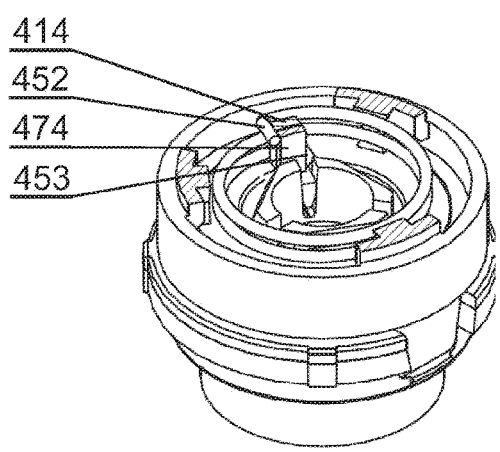
Figure 8G:
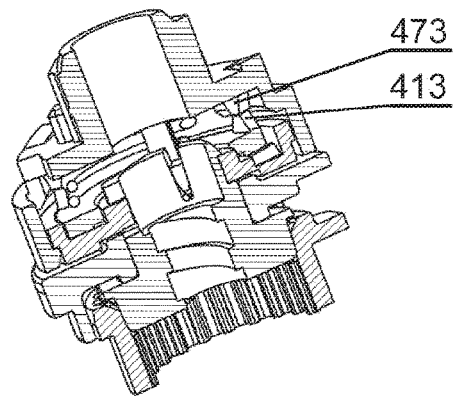
Figure 8H:
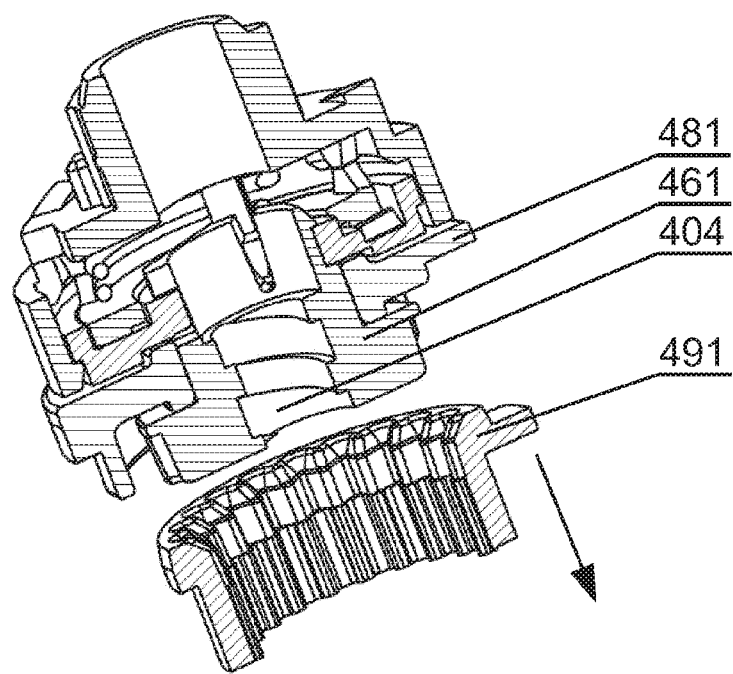

The rotation takes place as long as the user imparts force onto the dose setting element. When the user stops his action, the spring 451 by means of the curved end portions 452 and 453 causes lock of the device at the currently set value, i.e. it causes the protrusions 474 and 414 to return to their state of equilibrium. Lock of the assembly will be achieved by setting the locks 473 and 413 again opposite each other, as shown in FIGS. 8F and 8G.

The correcting motion takes place in an analogous manner, wherein it requires rotating the dose setting element by the user in a direction opposite to the dose setting direction. The forces accompanying both movements (setting and correcting) can be substantially equal.

After setting the dose it can be possible to trigger delivery of the dose by pushing the actuating member 491 downwards, what causes unblocking of the whole assembly, which due to the force of the driving spring starts rotating and by means of threaded connection with the piston rod 404 it will move it by a suitable value in the axial direction, which is shown in FIG. 8H.

In this embodiment, the housing 471 can be at the same time an element of the controlling assembly 410 which can be connected with a dose setting element, and at the same time it can be an element of the driving assembly 420, connected with the driving spring, which can be connected to the housing 471. The nut 461 together with the second coupling disc 421 can be the elements of the dosing assembly connected with the piston rod 404 for dosing the dose. The controlling assembly can be coupled with the dosing assembly by means of spring element 451, which during rotation of the dose setting knob undergoes deformation to the decoupled position and allows displacement of the controlling assembly with respect to the dosing assembly, and in the coupled position blocks the controlling assembly with respect to the dosing assembly.

In other words, in this embodiment the setting mechanism may comprise at least four rotatable elements (402, 411, 421, 451, 461, 471) connected to each other, wherein the rotatable elements (402, 411, 451, 471) can be rotatable during dose setting or reducing for a dosing device. The first rotatable element (411) can be a receiving element comprising corrugations, and the second rotatable element (421) may comprise corrugations cooperating with the corrugations of the first rotatable element, wherein said corrugations can be shaped so as to enable rotation of said at least four (402, 411, 421, 451, 461, 471) rotatable elements during dose delivering by the dosing device.

The mechanism can be sued in the applicator as discussed in FIGS. 1C, 1D—the elements indicated in FIGS. 7F and 7G can be equivalent to those shown in FIGS. 1C, 1D.

Embodiment

Figure 9A:
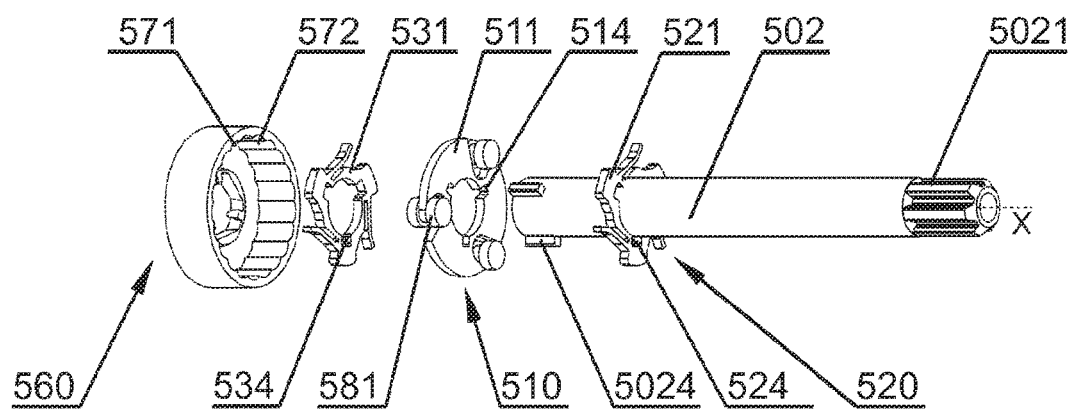
FIG. 9A show another embodiment of a mechanism.

FIG. 9A shows another embodiment of the mechanism, and FIGS. 10A-10H show its operation.

The mechanism may comprise a first coupling element. It can be the first coupling disc 511 (which can be called a returning disc), which can be coaxial with the main axis X of the mechanism and which can be connected with a dose setting element, for example in a form of a knob (not shown in this drawing). A connecting element 502 connects the disc 511 with the dose setting element. The connecting element 502 can be for example a rod, a sleeve, a cylinder or another suitably shaped element. The connection can be provided by the end part of the connecting element, in this example a first end part 5021 of the rod 502. On the second end part of the connecting element there can be protrusions 5024, which cooperate with recesses 514 of the first disc, in which they can be placed substantially without clearance.

The mechanism may comprise further a second and a third coupling element. In this embodiment it can be a second disc 521 (which can be called a driver disc) and the third disc 531, which can be coaxial with the main axis X of the mechanism and can be located on the opposite sides of the first disc 511. In other example there can be provided only one disc. The principle of operation will be discussed based on the second disc 521, it should be remembered that the third disc 531 performs analogous work. The second disc 521 may comprise a spring element 522, in this example an elastic arm, but it can be also another spring element, such as a torsion or compression spring. There can be recesses 524 and 534 in the discs 521, 531, cooperating with the protrusions 5024 in the connecting element 502 and transferring the torque from the dose setting element to the discs 521, 531. The recesses 524, 534 can be bigger than the protrusions 5024, thereby allowing free rotation of the connecting element 502 with respect to the disc 521, 531 in a certain limited range.

In the first disc 511 there can be corrugations in a form of recesses (tracks) 513, which in this embodiment can be preferably a through recesses in the disc 511. There can be located elements with shaped corrugations, preferably comprising matching recesses and bulges, providing contact through cooperating surfaces, preferably in a form of rolling elements 581. In this embodiment they comprise a cylinder with a recess (preferably providing a symmetry), shown as a core 582 in a form of a cylinder with a first diameter. Cylindrical heads 583, 584 can be located on the end parts of the core (preferably symmetrical with respect to each other) and have a second diameter, larger than the first diameter.

The first disc 511 with the rod 502 can be thus elements of the controlling assembly 510 of the mechanism.

The mechanism may also comprise a track 571 (which can be called a brake track), which can be coaxial with the main axis of the mechanism and can be corrugated inner surface of the cylindrical ring. This element may comprise shaped surfaces (they can be corrugated, e.g. sinusoidal, in a form of cam curvature or e.g. grooved), which can be substantially symmetric (the resistance of the contact surfaces can be therefore substantially equal). Consequently, a movement in one direction, as well as in the opposite direction (setting movement and reducing movement) can be accompanied by substantially equal force.

The recesses 572 of the track 571 have preferably a radius corresponding to the radius of the heads 583, 584 of the rolling elements 581. They may have also other form—a rack in the returning disc, a brake track and rolling element. A nut (not shown to simplify the drawing), for driving the dosing piston of the set dose, can be connected to the track 571. Thus, the track 571 can be an element of the dosing assembly 560.

The driving spring can be connected to the second disc 521 and/or to the third disc 531 directly or indirectly through an intermediary element. Thus, the second disc 521 and/or the third disc 531 can be an element of the driving assembly 520.

In this embodiment, the controlling assembly 510 can be thus coupled with the dosing device 560 by means of the spring element, which during rotation of the dose setting element deforms to the decoupled position and enables movement of the controlling assembly 510 with respect to the dosing assembly 560, and in the coupled position block the rotation of the controlling assembly 510 with respect to the dosing assembly 560.

In other words, in this embodiment the setting mechanism may comprise at least four rotatable elements (502, 511, 521, 531, 571, 581) connected with each other, wherein rotatable elements (502, 511, 521, 531, 581) can be rotatable during dose setting or reducing for the dosing device. The first rotatable element (511, 571) can be a receiving element and may comprise corrugations, and the second rotatable element (581) may comprise corrugations cooperating with corrugations of the first rotatable element, wherein said corrugations can be shaped so as to enable rotation of said at least four (502, 511, 521, 531, 571, 581) rotatable elements during dose delivering by the dosing device.

The mechanism according to this embodiment operates as follows.

The main principle of operation is analogous to the principle of operation of a unidirectional bearing, known also as a free wheel or a directional clutch. The unidirectional bearing mechanism can be used to transfer torque in one direction and allows for a free relative movement in the second direction. The rollers of the mechanism can be blocked (wedged) between outer ring and inner ring, and the working surfaces of these rings can be a self-locking angle. The rollers can be pushed individually to the track of the ring by means of pushing elements, for example springs and pushers, what causes immediate action, wherein the dead angle resulting only from the elastic deformations of the clutch elements is close to zero.

The mechanism according to this embodiment operates as follows.

During rotation in the dose setting direction the mechanism can freely move to subsequent angular positions. During rotation in the opposite direction—the reducing one, between the outer track, preferably in a form of a cylinder and the inner surface in a form of a section of an inclined plane there occurs a force wedging the working elements, such as rollers, balls or other elements enabling rolling, translation or rotation. The mechanism blocks instantly. By modifying this solution a lock effect of the mechanism can be achieved such that the driving spring strength cannot retract the set dose on its own.

Figure 10A:
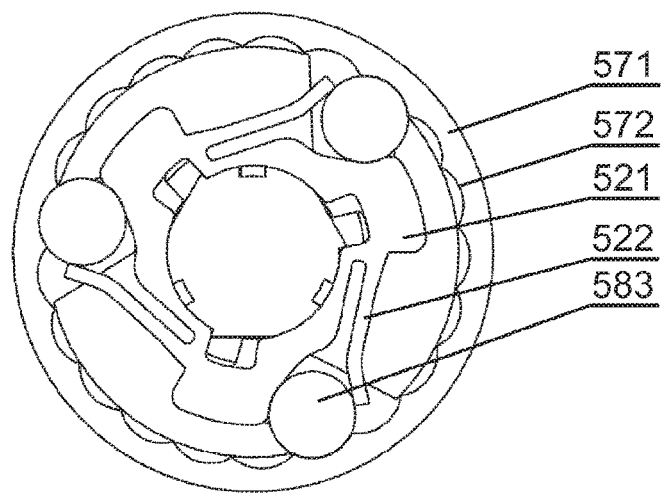
FIGS. 10A-10H show its method of operation.

Stopping the mechanism in a position every one dose can be enabled by the corrugated surface of the track 571 of the brake, the recesses 572 of which cause lock of the mechanism in certain positions, as shown in FIG. 10A.

Figure 10B:
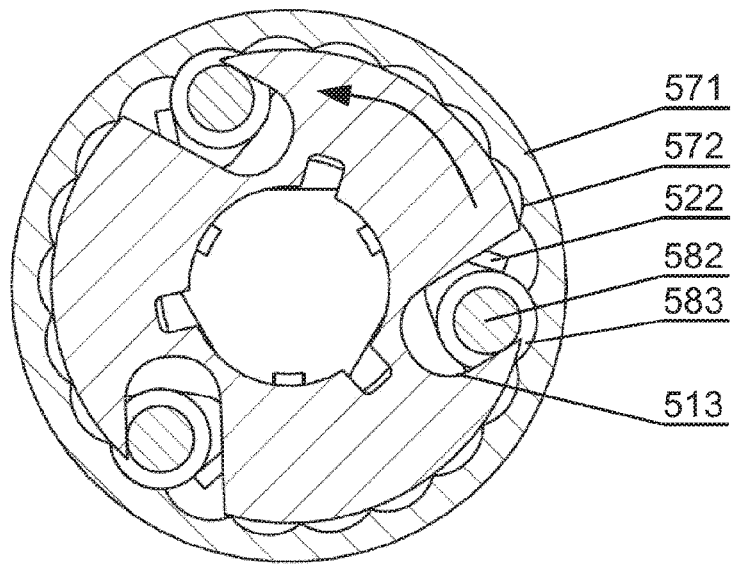
Figure 10C:
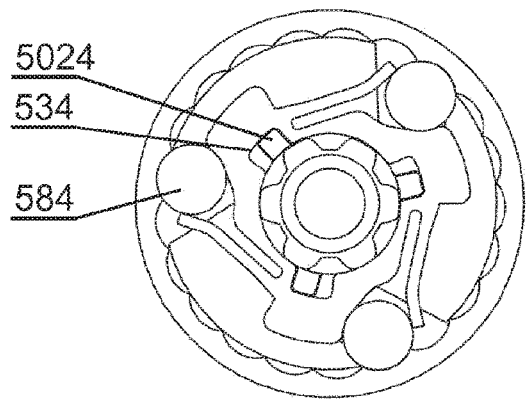
Figure 10D:
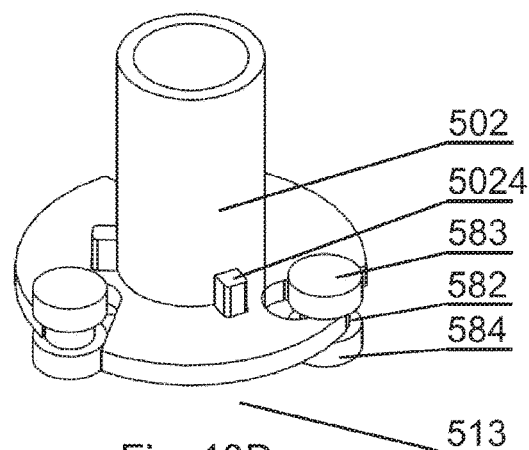

When the returning disc 511 moves in a direction indicated by the arrow in FIG. 10B, a pressure of the track 513 onto the smaller core 582 of the rolling element 581 can be caused, at the same time tensioning the spring element 522. The movement is possible, because the driving disc 521 and the returning disc 511 have different recesses 524, 514 cooperating with the protrusion 5024 of the connecting element 502, therefore their mutual position may change under the operation of the connecting element 502, as shown in FIGS. 10C and 10D. The driving disc 521 may comprise spring elements—in the form of elastic and flexible arms (which may be formed in different shapes or these can be different spring means, for example a spring, a bent material etc.).

Therefore the returning disk 511 can be connected with the connecting element 502 during the whole movement of the connecting element 502 in both directions, and the driving disc 521 can be connected with the connecting element 502 with a small clearance, so that the interrelation between them occurs only in one direction, compliant with the dose setting direction.

Figure 10E:
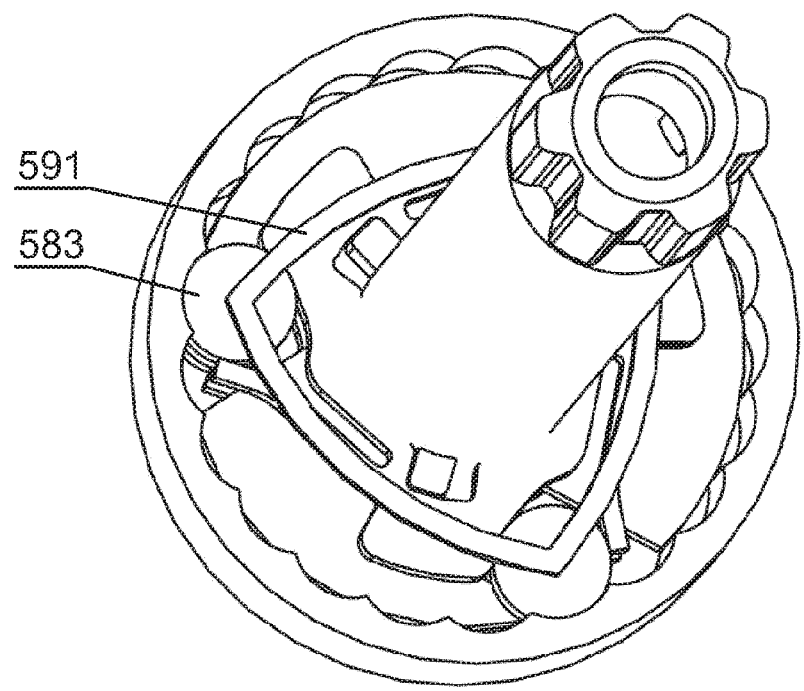

For simplification of manufacturing and assembly technology, the rolling elements 581 can be connected by a connecting element 591 as shown in FIG. 10E. During delivering the set dose the whole mechanism rotates, in particular after releasing the spring driving means. The nut also rotates.

The setting mechanism acts radially. In particular, the spring elements operate so that the elements with shaped corrugations, in particular the ones that block the mechanism (in this example—the rolling elements 581 can be polygonal, for example triangular, rhombus-shaped; can be coupled) move in the radial direction. They comprise surfaces cooperating with the rotatable element (driving disc of the driver, returning disc, track of the brake). Rotation of all the elements shown in FIG. 9A is ensured during injection.

During setting or reducing, the abovementioned elements rotate with exception of the track of the brake (it remains fixed with respect to the housing).

Figure 10F:
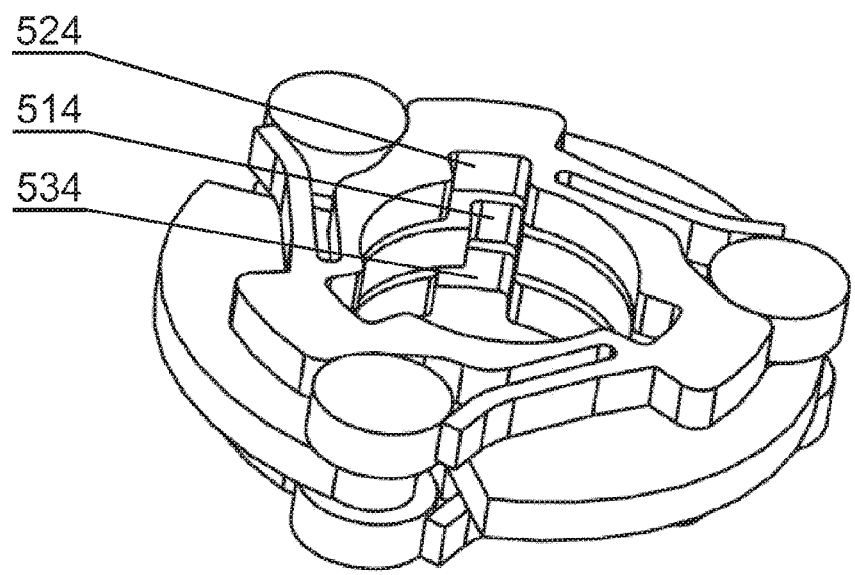
Figure 10G:
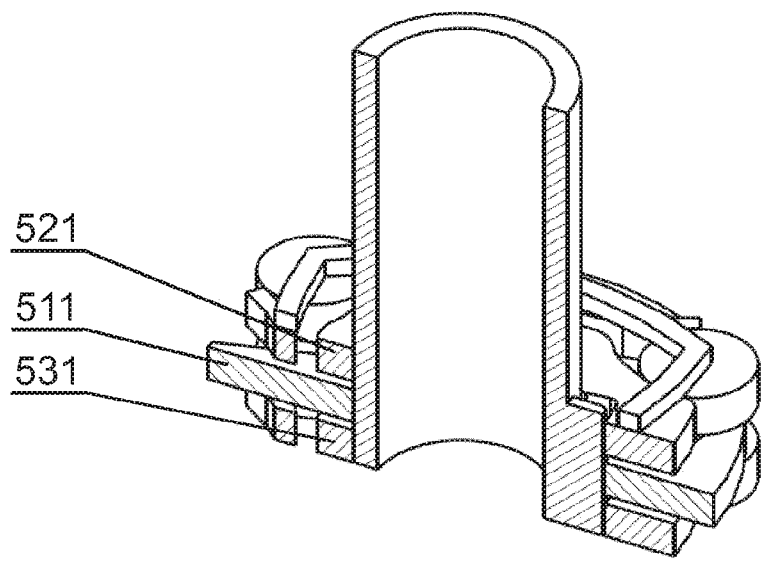
Figure 10H:
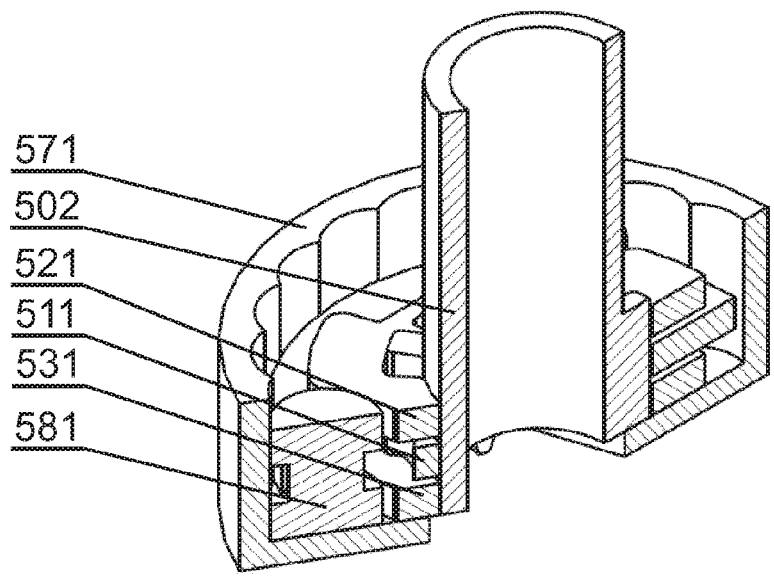
Figure 11A:
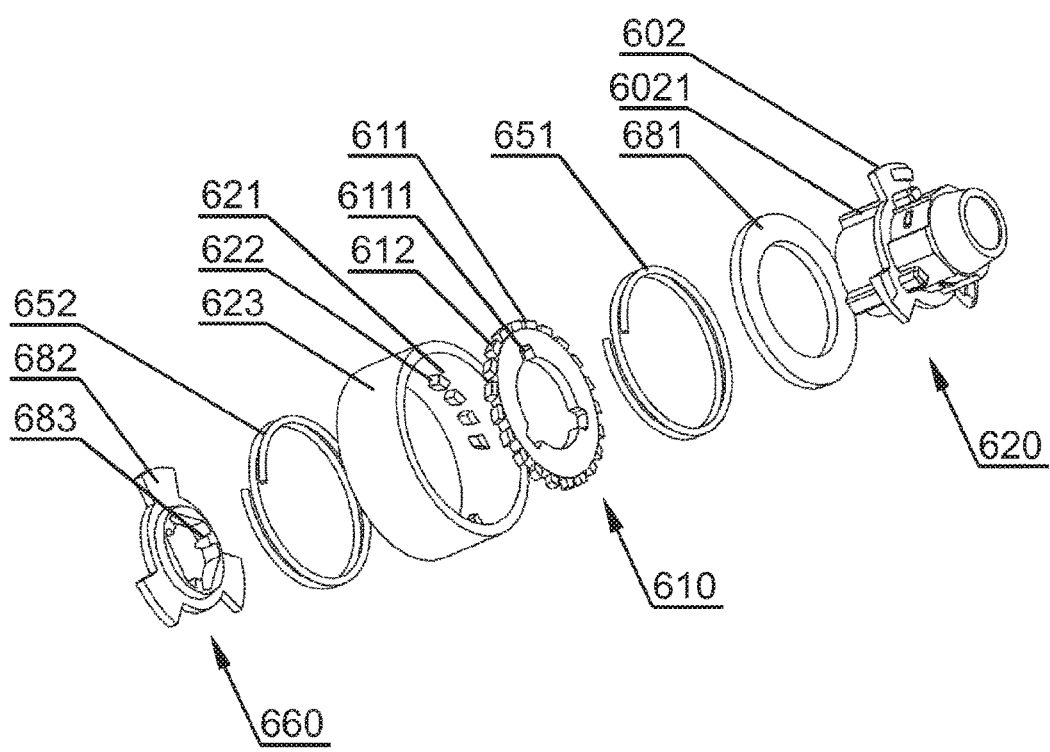
FIGS. 11A-11D show another embodiment of a mechanism.
Figure 11B:
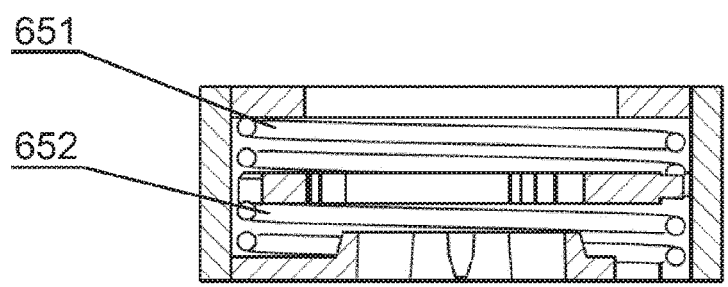
Figure 11C:
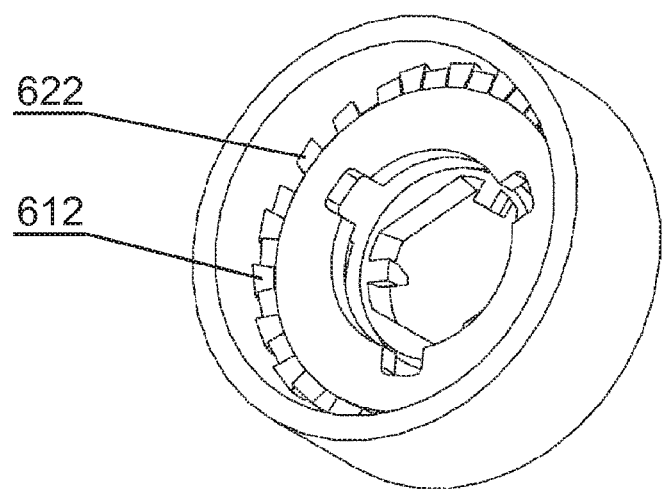
Figure 11D:
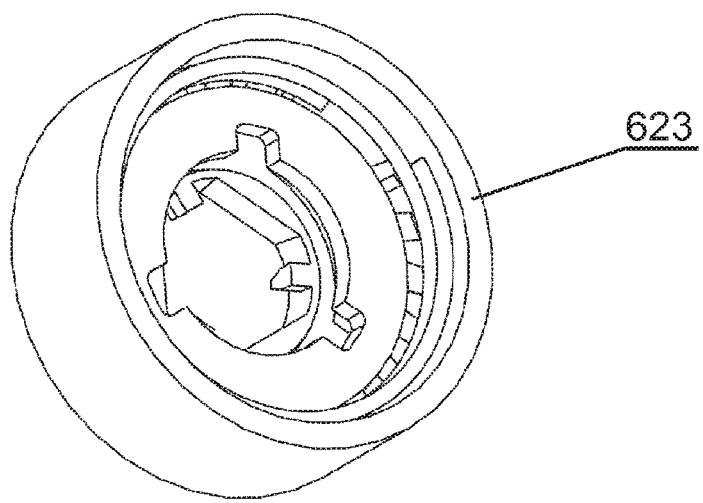

In this example, two driving disc 521, 531 can be used. This allows to additionally equalize forces acting on the rolling elements so that there is no buckling, as shown in FIGS. 10F-10H.

Embodiment

FIGS. 11A-11D show another embodiment of the mechanism, and FIGS. 12A-12E show its method of operation.

The mechanism may comprise a first coupling element. It can be a first movable element, preferably rotatable, preferably a coupling disc 611, which can be coaxial with the main axis X of the mechanism. The first coupling disc 611 can be connected with a dose setting element, for example in a form of a knob (not shown in this drawing). The dose setting element can be connected with the mechanism by means of a connecting element 602 in order to transfer force from a user to the mechanism. The connecting element 602 can be for example a rod, a sleeve, a cylinder or other suitably shaped element. The connecting element 602 and the first coupling disc 611 can be elements of controlling assembly 610. The controlling assembly 610 can be connected with the dose setting element, by means of which the user can choose or correct a dose to be applied. These elements can be connected by inlets/keys, protrusions or other means providing secure connection.

The connecting element 602 and the first coupling disc 611 can be separate elements, movable axially with respect to each other. In this example the first coupling disc 611 can be in a form of a ring with inlets 6111 formed in its inner track, which cooperate with longitudinal protrusions 6021 shaped at the end portion of the connecting element 602.

The mechanism may also comprise a second coupling element. It can be a second coupling disc 621, which can be coaxial with the main axis X of the mechanism. The second coupling disc 621 can be coupled with the first coupling disc 611. In this example, the element providing cooperation between the discs 621 and 611 can be corrugated elements, preferably in a form of shaped corrugations, preferably in a form of teeth 622 of the second coupling disc 621 directed in the opposite direction than teeth 612 of the first coupling disc 611 and engaged with them. In this embodiment the teeth 612, 622 protrude from disc in the axial direction. The shape of the teeth 622 of the second disc 621 must correspond to the shape of the teeth 612 of the first disc 611, but their count can be lower.

The driving spring (not shown in this drawing) can be connected to the connecting element 602, which can be an element of driving assembly 620. The driving spring can be connected to the driving assembly 620 directly or through additional connecting elements.

A nut (not shown in this drawing, which can be coupled with a shaped opening 624) can be connected, through a locking element 682 with the shaped opening 624, with the second coupling disc 621. The nut can be configured to rotate the piston rod dosing the set dose (not shown in this drawing). The second coupling disc 621 can be therefore an element of the dosing assembly 660 of the mechanism.

The second coupling disc 621 can be shaped on the inner surface of a cylindrical sleeve 623, of which the inlet and outlet can be limited by the locking elements 681, 682. Between the first coupling disc 611 and the locking elements 681, 682 there can be mounted pressing elements for holding the first coupling disc 611 in a middle position, coupled with the second coupling disc 621, but allowing it to decouple in both axial directions along the main axis X of the mechanism. In this example, the pressing elements can be compression springs 651, 652, but the pressing elements can be also another type of a spring element, being a separate element or an integral component of at least one of the other elements. For example, it can be resilient protrusions formed in the first coupling disc 6111 or other elements.

In this embodiment, the controlling assembly 610 can be therefore coupled with the dosing assembly 660 by means of the spring elements 651, 652, which during rotation of the dose setting knob deform to decoupled position and allow movement of the controlling assembly 610 with respect to the dosing assembly 660, and in the coupled position they block rotation of the controlling assembly 610 with respect to the dosing assembly 660.

The springs 651 and 652 can rotate during dose setting or correcting. They can be also integral with the element 611 (in such case, they rotate simultaneously); alternatively, they can be also integral with the elements 681 and 682 (in such case, they will not rotate during dose setting or correcting).

In other words, in this embodiment the setting mechanism may comprise at least four rotatable elements (602, 611, 621, 651, 652, 681, 682) connected with each other, wherein the rotatable elements (602, 611, 651) can be rotatable during dose setting or reducing for the dosing device. The first rotatable element (611) can be a receiving element and may comprise corrugations, and the second rotatable element (621) may comprise corrugations cooperating with corrugations of the first rotatable element, wherein said corrugations can be shaped so that they enable rotation of said at least four (602, 611, 621, 651, 652, 681, 682) rotatable elements during dose delivering by the dosing device.

The mechanism according to this embodiment operates as follows.

The first coupling disc 611 is in its resting position coupled with the second coupling disc 621 and the discs can be held in this state by the springs 151, 152, which at the same time press from both sides on both discs 611, 621. Because only the first disc 611 can move axially, such engaged assembly remains in state of equilibrium, shown in FIG. 12E. On the other hand, all elements in FIG. 11A remain rotatable (in particular, during injecting).

Figure 12A:
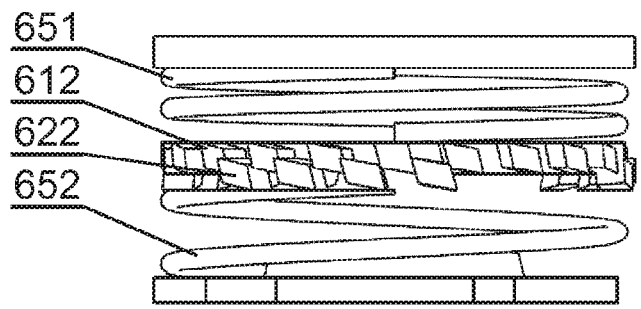
FIGS. 12A-12E show its method of operation.
Figure 12B:
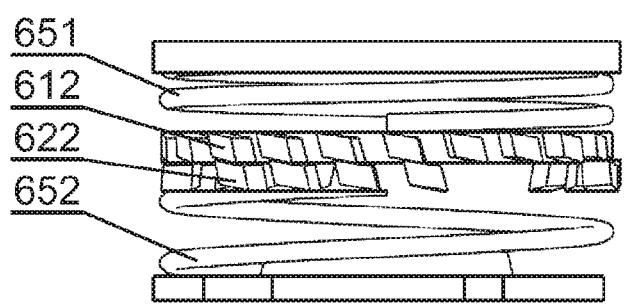
Figure 12C:
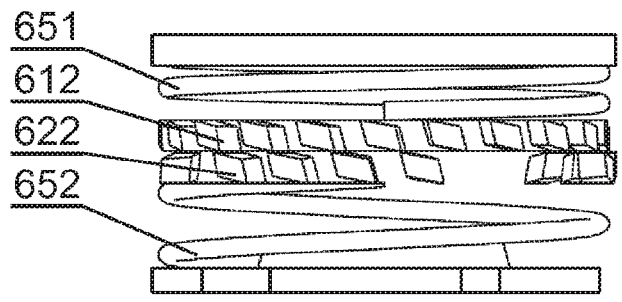
Figure 12D:
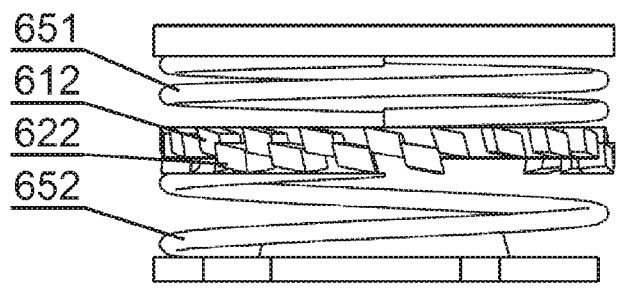
Figure 12E:
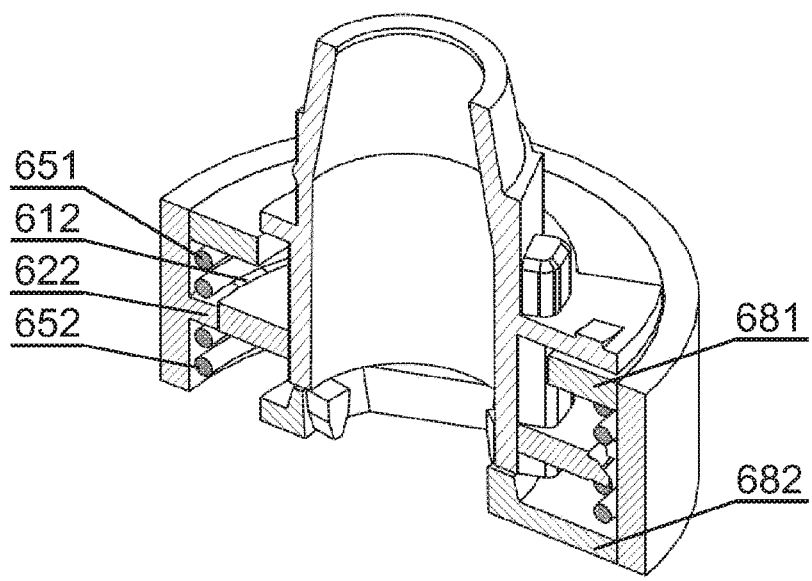

The discs 611, 621 comprise teeth contact surfaces 612, 622 in between them at certain angle. During dose setting by means of rotation of the coupling element 602 in one direction, indicated by movement between FIG. 12A and FIG. 12B, there occurs compression of one spring 652 (wherein the spring 651 does not deform in this case) and the first disc 611 moves axially in the direction of compression of this spring 652 (FIG. 12B) until the moment of decoupling with the second disc 621 (FIG. 12C). During further rotation of the mechanism, the spring 652 causes the first disc 611 to move away to the initial position and to couple on further teeth of the disc (FIG. 12D).

Movement in the opposite direction can be analogous, but it requires rotating the coupling element 602 in the opposite direction, which causes movement of the first disc 611 in the direction, in which it will cause compression of the second spring 651 (wherein the spring 652 does not deform). Configuration of the rotatable elements can be responsible for equal (substantially) force acting in the dose setting direction and in the opposite direction. In particular, cooperation of the two springs with element 610 can be substantially equal (i.e. the pressing can be equal, independently of the direction). Any possible differences in force could thus be caused by purposeful selection of spring means of differentiated characteristics.

Further Embodiments

There are possible further embodiments, comprising an arrangement of elements two or more of the above-described embodiments.

Further, the rotatable elements can be a disc, a rim, a disc, a ring, a hoop, a roller, a sleeve, a circular element or other form of a shaped element enabling a rotation, irregular or non-circular forms included.

Further, the corrugations (substantially regular) in corrugated elements may have a form of teeth, deformations, ridges, curvatures, cams, inlets, protrusions, horsts, recesses, indentations, reliefs, cut-outs, notches, grooves, curvatures, claws/centers, pinions, ribs, catchs/dogs, inlets, protrusions or threads. They can be trapezoid, V-shaped, triangular, curved, sinusoidal.

The corrugations can be configured to abut each other at least partially, thereby providing rotation of one corrugated element by the abutting corrugated element.

The corrugations can be configured so that substantially the same force is needed for dose setting and dose correcting, both in case of symmetric and asymmetric shape.

The corrugations can form a latch, they can also be non-latching, with clearance or without clearance, frictional or interferential type, connected vertically or horizontally, axially, forwardly or radially.

The corrugated elements can be movable, including rotatable, axially, forwardly and radially.

The corrugated elements can be coaxial.

The corrugated elements can be symmetrical or asymmetrical.

The corrugated elements may have differentiating ridges.

The corrugated elements may comprise connecting elements, connecting protrusions. They may comprise any shapes configured for connecting and coupling upon contact.

The corrugated elements can be located on discs constituting separate elements or on the housing of other elements of the mechanism, or on the housing of the device for injecting, or other cooperating element.

The corrugations can be located on the outer or inner surface of the element.

The cooperating corrugated elements may have an equal (corresponding) amount of corrugations or a different amount.

The cooperating corrugated elements may have corrugations of the same or of a different shape.

The direction of corrugations indicated in respective examples can be changed, preferably to the opposite one.

The mechanism may comprise at least two rows or series of corrugated elements. The corrugations of at least two rows or series of the corrugated elements may have different height, different inclinations or different amplitude or period. At least two rows, series or rings of corrugated elements may have different coupling strengths. In a particular case, the coupling strength of corrugated elements is equal.

The number of corrugations on one corrugated surface can be a multiplicity of the number of corrugations on the cooperating second corrugated surface, for example if on one surface there can be 7 corrugations, then on the second surface there may be 7, 14, 21 etc. corrugations.

The locations of corrugations on the cooperating elements can be interchangeable (in particular, when they differ in the number of corrugations, e.g. in case of connections of mutually dividable corrugations, as discussed above).

The configuration of the rotatable elements, including those comprising corrugated elements, enables connections defining substantially equal force during setting and/or correcting. Deviations and differentiations can result from e.g. precision of manufacturing and assumed (or real) tolerances of particular components of the dosing device, occurring additional resistances (e.g. uneven wearing of the elements) or cooperation with other elements in the device.

The coupling discs can assume any engagement positions, constituting or cooperating with at least one receiving surface (frictional, latching).

The spring element of the mechanism can be any spring means, such as a torsion spring, compression spring, disk spring, clock spring, plate spring, rebound spring, bent plate (suspension spring), flat spiral spring, a formed elastic element of material with elastic properties, etc.

The coupling between the elements of the mechanism may have various forms, for example there can be a claw/dog coupling between the elements. Also, the coupling mechanism can be as shown in U.S. Pat. No. 2,667,252 publication. The coupling can thus comprise at least three cooperating rotatable elements, including at least one disc.

In the device for injecting the actuating member is to be understood as any dosing activating means, in a form of releasing means, lock means, latching means, in particular a button, a trigger, a trigger on the side wall of the device.

The button can be movable between passive and active positions—moving it to the active position can cause a rotation of the dose indicator in a direction of the zero dose and dose injection. A return of the button to the passive position can cause the end of dose injecting.

The device may comprise various types of dose indicators, including indicators of a digital type, a number type, a letter type or in a form of a line, positioned along a circle or a helix, on a threaded scale or slidably moving, as a counting wheel.

Dose expelling in the device can be carried out by elements, mechanisms or driving members, using single elements or their arrangements, including driving nuts. The driving nut can be rotatable or movable axially. The piston rod driven by the nut can be movable axially, or movable and rotatable.

The device for injecting according to at least one of the discussed examples can be used as follows. A cap of the injector should be taken off. A cartridge shield should be unscrewed anticlockwise from the housing of the injector. The insertion shield should be screwed to the housing of the injector clockwise. An outer needle shield should be screwed clockwise to the insertion shield. If priming is required, the dose setting element should be rotated clockwise. When a certain number shows in the dose indicating window (for example, 2 units), the rotation of the dose selector ends. The injector should be set so that the needle points upwards. The actuating member should be moved towards the needle with a thumb. The actuating member should be held until the indicator (e.g. in a form of a green dot) shows in a window of the injection end signaler. If no insulin drop appears at the end of the needle, the activities are repeated. If no drop appears after a few attempts, the needle should be removed and a new needle should be mounted. A test dose should be set before a first use of the injector after replacing the cartridge. In order to do that, the dose setting element should be rotated clockwise, until the desired number appears in the window, which corresponds to the liquid preparation units count. If one selects an excessive number of units, the dose can be corrected. The end of the needle should be inserted into the subcutaneous tissue. The actuating member should be pushed towards the needle with a thumb. The actuating member should be held until the end of the injection. The end of the injection can be indicated by appearance of the indicator (e.g. a green dot) in the signaler window. The user waits for a specified amount of time, for example by counting to 10. At the end, the needle should be taken out.

The invention claimed is:

1. An applicator comprising:
   a housing comprising an inspection opening,
   a dose setting knob coupled to the housing,
   a setting mechanism coupled by a connecting element to the dose setting knob,
   at least two coil springs comprising a driving coil spring extending in an axial direction,
   a non-rotatable lock connected to the housing and to the driving coil spring,
   a rotatable driving sleeve connected to the driving coil spring,
   an indicating sleeve connected movably with the rotatable driving sleeve,
   wherein the indicating sleeve is mounted slidingly and co-axially on the rotatable driving sleeve by a spline coupling comprising longitudinal protrusions,
   wherein the housing comprises a first end portion with a first external diameter and a second end portion with a second external diameter, the second external diameter being greater than the first external diameter,
   wherein the dose setting knob is rotatable and comprises at least one protrusion to couple with the first end portion of the housing,
   wherein the connecting element comprises a longitudinal sleeve and extends above the first end portion of the housing to couple with the dose setting knob,
   wherein the first end portion of the housing comprises at least two openings arranged non-coaxially,
   wherein the non-rotatable lock comprises a curved surface to cover at least a portion of the at least two openings of the first end portion of the housing,
   wherein the non-rotatable lock comprises a through-bore to receive the longitudinal sleeve of the connecting element, an opening to attach the driving coil spring and a wall to separate at least partially the through-bore from the opening,
   wherein the wall of the non-rotatable lock covers at least a portion of the longitudinal sleeve of the connecting element,
   wherein the longitudinal sleeve of the connecting element comprises a first end portion comprising protrusions and a second end portion to receive at least a portion of a piston rod,
   wherein the piston rod is coupled to the driving coil spring, the driving coil spring being configured to drive the piston rod,
   wherein the dose setting knob covers at least a portion of the wall of the non-rotatable lock, the curved surface of the non-rotatable lock, the first end portion of the housing and the protrusions of the first end portion of the longitudinal sleeve of the connecting element,
   wherein the dose setting knob, the housing, the non-rotatable lock, the driving sleeve, the indicating sleeve, the driving coil spring, the connecting element and the piston rod are arranged coaxially.

2. The applicator according to claim 1, wherein the longitudinal sleeve of the connecting element comprises an internal waist.

3. The applicator according to claim 1, wherein the at least one protrusion of the dose setting knob axially blocks the dose setting knob to prevent the dose setting knob from moving in the axial direction.

4. The applicator according to claim 1, wherein the dose setting knob comprises at least one through-bore comprising a first opening and a second opening.

5. The applicator according to claim 4, wherein the dose setting knob comprises a covering element, wherein the covering element covers at least the first opening of the at least one through-bore of the dose setting knob, wherein the covering element comprises at least one protrusion and a concave portion.

6. The applicator according to claim 1, wherein the the applicator comprises the indicating sleeve and a cartridge holder, wherein only one of the indicating sleeve and the cartridge holder comprises a scale.

7. The applicator according to claim 1, wherein the the applicator comprises a cartridge holder, wherein the cartridge holder comprises an opening window, wherein the opening window comprises opposite edges, wherein the opposite edges are symmetrically shaped in respect to a main axis of the applicator.

8. The applicator according to claim 1, wherein the housing comprises at least five openings.

9. The applicator according to claim 1, wherein the dose setting knob, the connecting element, the driving sleeve, the indicating sleeve and the driving coil spring are rotatable.

10. The applicator according to claim 1, wherein the spline coupling ensures a play between an outer cylinder of the driving sleeve and an inner cylindrical wall of the indicating sleeve.

11. The applicator according to claim 1, wherein the piston rod is coupled to a piston rod guide and a nut.

12. The applicator according to claim 6, wherein the cartridge holder comprises an external surface, a first portion, a second portion and a third portion, wherein the first portion of the cartridge holder is adapted to connect with a needle, the second portion of the cartridge holder comprises an opening window and the third portion of the cartridge holder is adapted to connect with the housing, wherein only one of the first portion of the cartridge holder and the second portion of the cartridge holder comprises grooves on the external surface.

13. The applicator according to claim 1, wherein the indicating sleeve covers at least a portion of the rotatable driving sleeve, the rotatable driving sleeve covers at least a portion of the driving coil spring, and the driving coil spring covers at least a portion of the connecting element.

14. The applicator according to claim 1, wherein the setting mechanism comprises a controlling assembly for connecting the setting mechanism with the dose setting knob, a driving assembly for connecting the setting mechanism with the spring element, a dosing assembly for connecting the setting mechanism with the piston rod, wherein the piston rod is connected to a nut, wherein the piston rod or the nut is rotatable.

15. The applicator according to claim 1, wherein the inspection window is at least partially surrounded by an indentation portion of the housing, wherein the indentation portion comprises at least two protrusions.

16. The applicator according to claim 1, wherein the applicator comprises a cap, wherein the cap comprises a proximal portion and a distal portion, wherein the proximal portion comprises an external surface, wherein the cap comprises at least three hollow portions on the external surface of the proximal portion.

17. The applicator according to claim 1, wherein the applicator is adapted to provide a substantially constant time of injection for a particular dose.

18. The applicator according to claim 1, wherein the applicator is adapted to administer GLP-1, wherein the applicator is adapted to hold a 1.5 mL cartridge.

19. The applicator according to claim 1, wherein the applicator is an injecting device for liquid preparations, wherein an injection force of the applicator does not exceed 10 N.

20. The applicator according to claim 1, wherein the applicator is a delivery device adapted to inject 20 IU within a range from 0.9 seconds to 1.8 seconds.

* * * * *